United States Patent
Sasago et al.

(10) Patent No.: US 10,466,198 B2
(45) Date of Patent: Nov. 5, 2019

(54) GAS SENSOR

(71) Applicant: HITACHI, LTD., Tokyo (JP)

(72) Inventors: Yoshitaka Sasago, Tokyo (JP);
Toshiyuki Usagawa, Tokyo (JP);
Hitoshi Nakamura, Tokyo (JP)

(73) Assignee: HITACHI, LTD., Tokyo (JP)

( * ) Notice: Subject to any disclaimer, the term of this patent is extended or adjusted under 35 U.S.C. 154(b) by 182 days.

(21) Appl. No.: 15/788,308

(22) Filed: Oct. 19, 2017

(65) Prior Publication Data
US 2018/0120253 A1 May 3, 2018

(30) Foreign Application Priority Data
Oct. 28, 2016 (JP) .................................. 2016-212043

(51) Int. Cl.
| | |
|---|---|
| *G01N 27/414* | (2006.01) |
| *H01L 29/78* | (2006.01) |
| *H01L 29/49* | (2006.01) |
| *H01L 23/34* | (2006.01) |
| *H01L 29/08* | (2006.01) |
| *H01L 29/10* | (2006.01) |

(52) U.S. Cl.
CPC ..... *G01N 27/4141* (2013.01); *H01L 29/4966* (2013.01); *H01L 29/78* (2013.01); *H01L 23/345* (2013.01); *H01L 29/0847* (2013.01); *H01L 29/1095* (2013.01)

(58) Field of Classification Search
CPC . G01N 27/4141; H01L 29/4966; H01L 29/78; H01L 29/0847
See application file for complete search history.

(56) References Cited

U.S. PATENT DOCUMENTS

2011/0113859 A1* 5/2011 Anthopoulos ...... H01L 29/4908
73/31.06
2017/0168000 A1* 6/2017 Ichiki ...................... H01L 21/28

FOREIGN PATENT DOCUMENTS

JP 2016-085124 A 5/2016

OTHER PUBLICATIONS

Hubert, T., et al, "Hydrogen sensors—A review," Sensors and Actuators B: Chemical, Elsevier, 2011, B157, pp. 329-352.
Miyahara, Y, et al., "Field-effect transistor using a solid electrolyte as a new oxygen sensor," AIP Journal of Applied Physics, 1988, 63, pp. 2431-2434.

* cited by examiner

*Primary Examiner* — Paul M. West
(74) *Attorney, Agent, or Firm* — Volpe and Koening, P.C.

(57) ABSTRACT

In a gas sensor using a first FET-type sensor for a sensor unit, a gas density measurement unit measures a gas density of gas to be detected at a predetermined time on the basis of a first threshold change as a difference between a first threshold voltage applied to a first gate layer when a first source-drain current is a first threshold current while the gas to be detected is not present in the atmosphere and a second threshold voltage applied to the first gate layer when the first source-drain current is the first threshold current at the predetermined time while the gas to be detected is present in the atmosphere, and a temporal differentiation of the first threshold change.

15 Claims, 21 Drawing Sheets

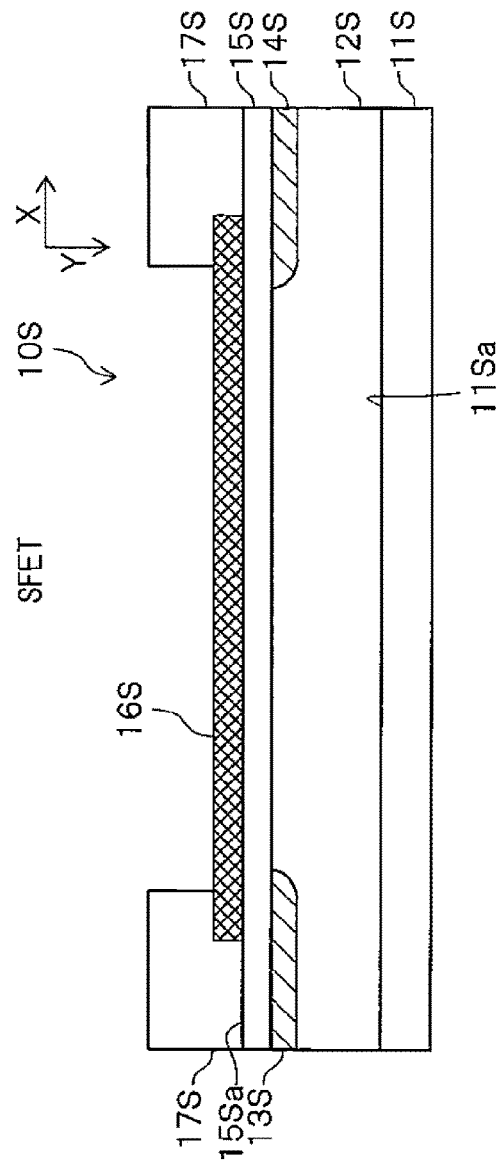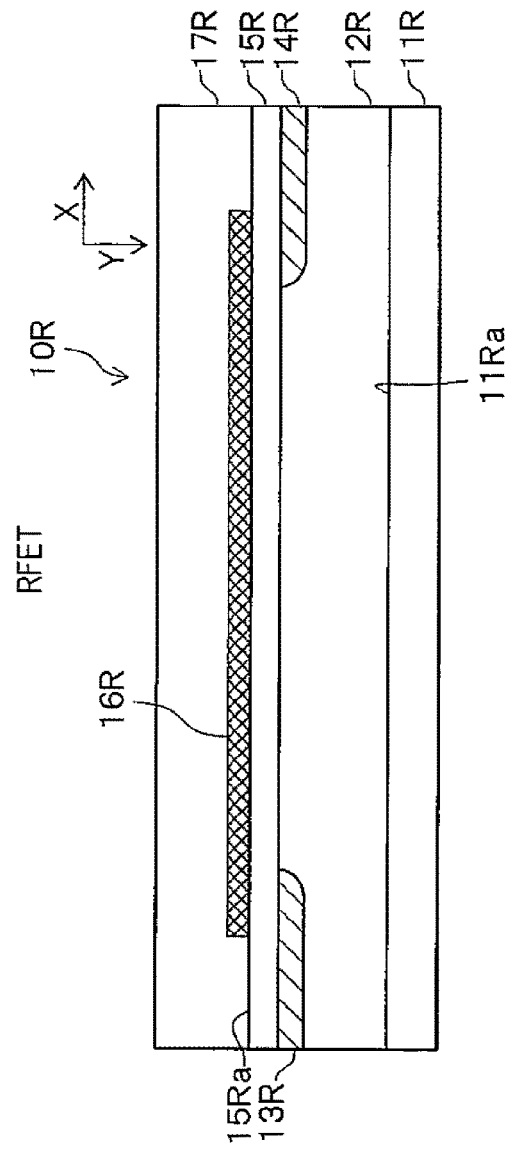

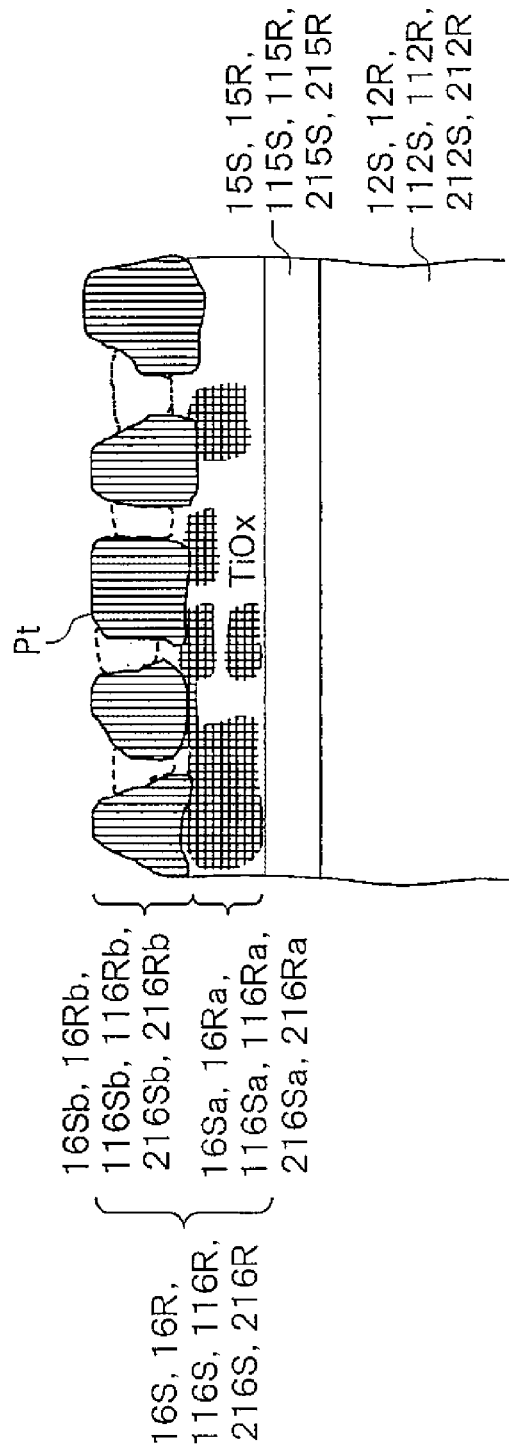

GAS SENSOR

BACKGROUND OF THE INVENTION

1. Field of the Invention

The present invention relates to a gas sensor.

2. Description of the Related Art

A gas sensor is provided on a gas densitometer, leakage detector, and the like, and is directed for measuring a gas density of hydrogen, methane, nitrogen oxide, hydrogen sulfide, or carbon monoxide. Gas sensors of contact burning-type, gas heat conduction-type, and the like have been known, for example.

Additionally, gas sensors manufactured in a semiconductor process have been recently put to practical use. For example, "Sensors and Actuators," 2011, B157, p. 329-352 discloses gas sensors of field effect transistor (FET) type, capacitor type, and diode type as gas sensors for hydrogen gas. Further, JP 2016-85124 A discloses a gas sensor capable of correcting an effect of radiation and accurately measuring a hydrogen gas density. Further, "Journal of Applied Physics," 1988, 63, p. 2431-2434 discloses a FET-type gas sensor for measuring a gas density of oxygen gas.

The gas sensors of FET type, capacitor type, and diode type can be manufactured in a semiconductor process using a semiconductor wafer. Thus, the gas sensors are expected to be lower in cost, smaller in size, and lower in power consumption than the gas sensors of other systems.

SUMMARY OF THE INVENTION

In many cases, a gas sensor is required to measure a change in density of gas to be detected in a short response time. For example, a gas sensor provided in a hydrogen leakage detector for fuel-cell vehicle is required to respond to a change in density of hydrogen gas within one second. The gas sensors of contact burning-type and gas heat conduction-type are directed for detecting a gas density by use of heat, and can respond to a change in density of gas to be detected within a short time.

On the other hand, a chemical reaction such as adsorption/decomposition of gas to be detected is performed in a material layer and thus a work function of the material layer changes in a gas sensor manufactured in a semiconductor process. A gas density is measured on the basis of a resultant threshold change of the gas sensor. The chemical reaction in the material layer proceeds to reach an equilibrium state, and the gas density is measured on the basis of the threshold change in the equilibrium state.

It may take several seconds or more for the chemical reaction to reach the equilibrium state, or several tens of seconds or several hundred seconds or more depending on circumstances. Thus, the gas sensor cannot measure a gas density in a short time while waiting for the equilibrium state to be reached.

It is therefore an object of the present invention to provide a gas sensor capable of measuring a gas density in a short time.

An outline of a representative invention among the inventions disclosed in the present application will be briefly described below.

A representative gas sensor according to an embodiment of the present invention includes: a sensor unit including a first field-effect-transistor (FET)-type sensor, the first FET-type sensor including: a first semiconductor substrate; a first well formed on the first semiconductor substrate; a first source diffusion layer formed on the first well; a first drain diffusion layer formed on the first well; a first gate insulative film formed on the first source diffusion layer and the first drain diffusion layer; and a first gate layer formed on the first gate insulative film in which at least part of a surface opposing the atmosphere is exposed; a current measurement unit for measuring a first source-drain current flowing between the first source diffusion layer and the first drain diffusion layer; and a gas density measurement unit for measuring a gas density of gas to be detected in the atmosphere, wherein the gas density measurement unit measures the gas density of the gas to be detected at a predetermined time on the basis of a first threshold change as a difference between a first threshold voltage applied to the first gate layer when the first source-drain current is a first threshold current while the gas to be detected is not present in the atmosphere and a second threshold voltage applied to the first gate layer when the first source-drain current is the first threshold current at the predetermined time while the gas to be detected is present in the atmosphere, and a temporal differentiation of the first threshold change.

The effects obtained by the representative invention among the inventions disclosed in the present application will be briefly described below.

That is, it is possible to measure a gas density in a short time.

BRIEF DESCRIPTION OF THE DRAWINGS

FIGS. 2A and 2B are cross-section views illustrating exemplary configurations in a sensor unit according to the first embodiment of the present invention;

FIG. 3 is a cross-section view illustrating an exemplary configuration of a gate layer in the sensor unit according to the first embodiment of the present invention;

DESCRIPTION OF THE PREFERRED EMBODIMENTS

Figure 1:
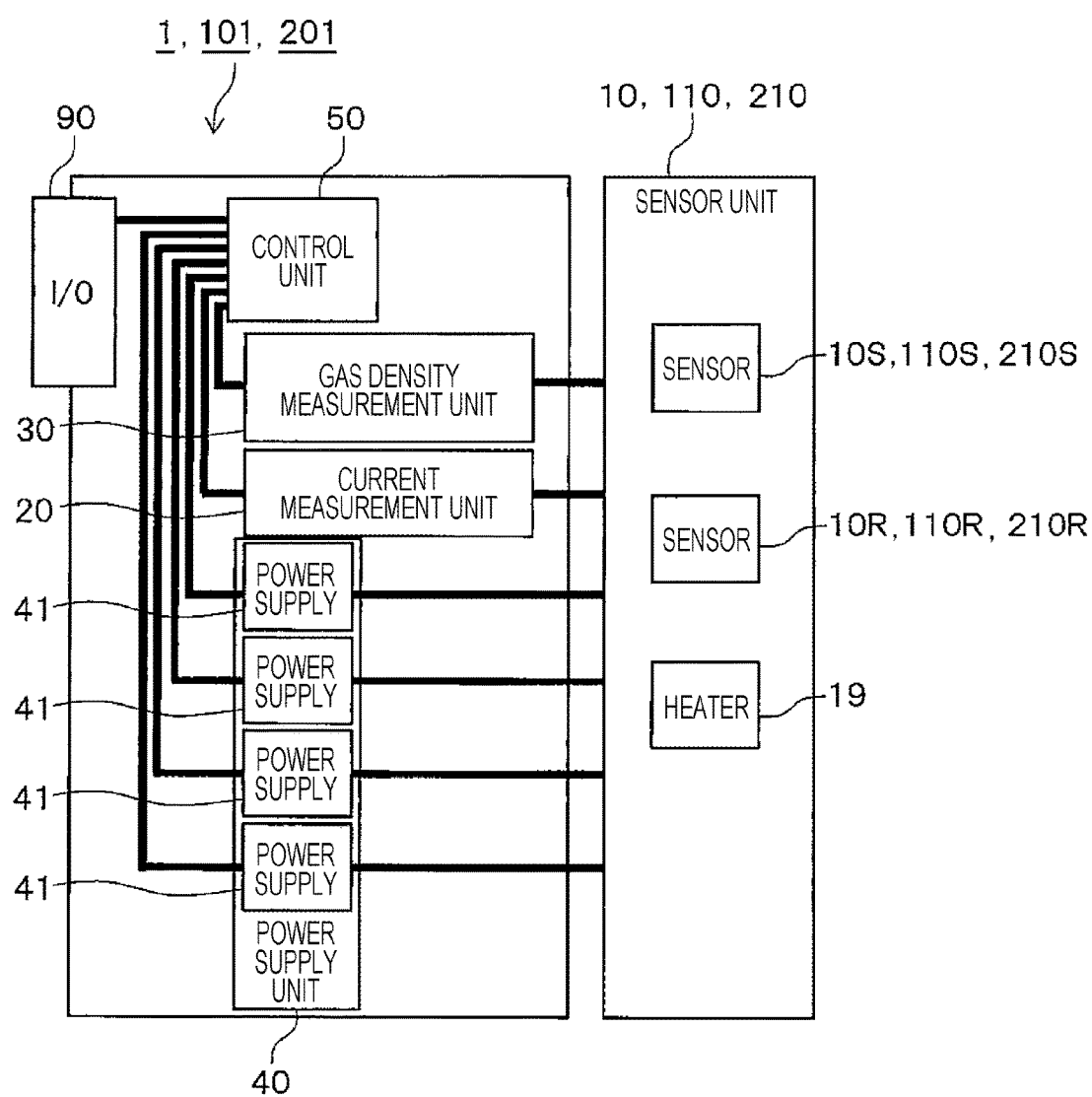
FIG. 1 is a diagram illustrating an exemplary configuration of a gas sensor according to a first embodiment of the present invention.

Embodiments of the present invention will be described below with reference to the drawings. The same parts are basically denoted with the same reference numerals in all the drawings for describing the embodiments, and a repeated description thereof will be omitted.

First Embodiment

<Configuration of Gas Sensor>

Figure 4A:
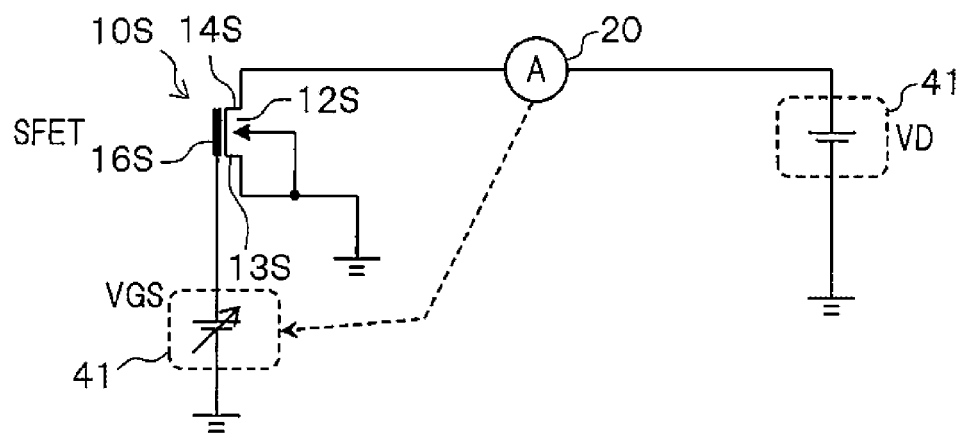
FIGS. 4A to 4C are diagrams illustrating exemplary connection configurations in the sensor unit according to the first embodiment of the present invention.
Figure 4B:
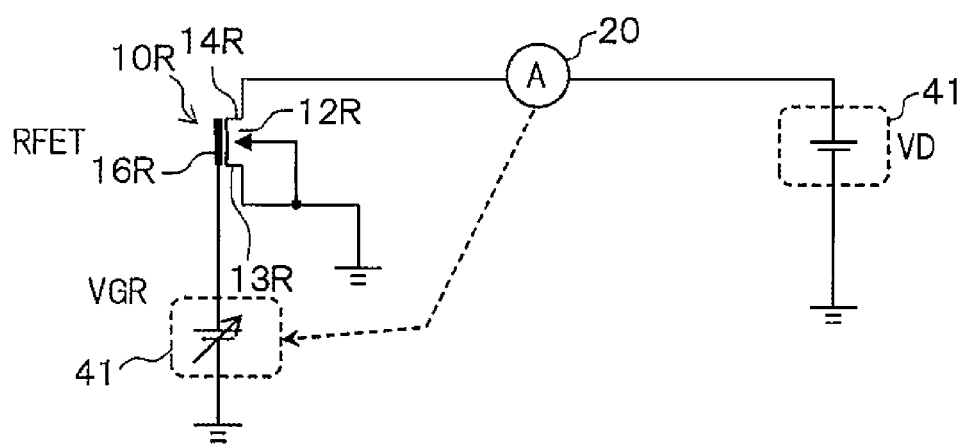
Figure 4C:
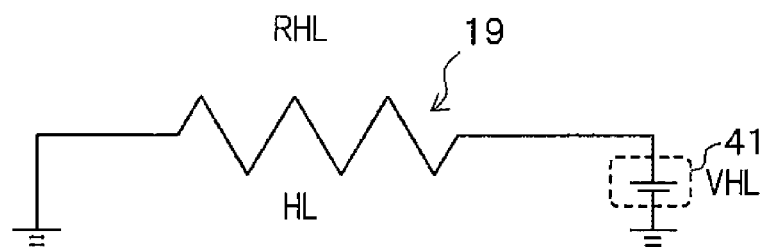

FIG. 1 is a diagram illustrating an exemplary configuration of a gas sensor according to a first embodiment of the present invention. FIGS. 2A and 2B are cross-section views illustrating exemplary configurations in a sensor unit according to the first embodiment of the present invention. FIG. 2A is a cross-section view of a sensor (first FET-type sensor) 10S and FIG. 2B is a cross-section view of a sensor (second FET-type sensor) 10R. FIG. 3 is a cross-section view illustrating an exemplary configuration of a gate layer in the sensor unit according to the first embodiment of the present invention. FIGS. 4A to 4C are diagrams illustrating exemplary connection configurations in the sensor unit according to the first embodiment of the present invention. FIG. 4A is a diagram illustrating an exemplary connection configuration of the sensor 10S. FIG. 4B is a diagram illustrating an exemplary connection configuration of the sensor 10R. FIG. 4C is a diagram illustrating an exemplary connection configuration of a heater 19.

As illustrated in FIG. 1, a gas sensor 1 includes a sensor unit 10, a current measurement unit 20, a gas density measurement unit 30, a power supply unit 40, a control unit 50, and a data I/O unit 90. The sensor unit 10 includes the sensors 10S and 10R, and the heater 19 as illustrated in FIG. 1.

The sensor 10S includes a semiconductor substrate (first semiconductor substrate) 11S, a well (first well) 12S, a source diffusion layer (first source diffusion layer) 13S, a drain diffusion layer (first drain diffusion layer) 14S, a gate insulative film (first gate insulative film) 15S, a gate layer (first gate layer) 16S, and a gate protective film (first gate protective film) 17S as illustrated in FIG. 2A. The semiconductor substrate 11S is made of silicon (Si) or silicon carbide (SiC), for example.

The well 12S is formed on a main surface 11Sa of the semiconductor substrate 11S as illustrated in FIG. 2A. The well 12S is formed by implanting therein a predetermined impurity defining the characteristic of the sensor 10S. The well 12S is an N-type or P-type layer, for example. The well 12S is formed to surround the source diffusion layer 13S, the drain diffusion layer 14S, the gate insulative film 15S, the gate layer 16S, and the gate protective film 17S, which will be described below, in the plan view (in the Y-axis direction), for example.

The source diffusion layer 13S is formed over the semiconductor substrate 11S as illustrated in FIG. 2A. As illustrated in FIG. 2A, the source diffusion layer 13S is formed to cover part of the well 12S in the plan view (in the Y-axis direction), for example. The source diffusion layer 13S is formed to cover the left side of the well 12S (on the negative side of the X-axis), for example. The source diffusion layer 13S is formed by implanting therein a predetermined impurity defining the characteristic of the sensor 10S. The source diffusion layer 13S has a different conductive type from the well 12S in the N-type or P-type layer, for example. For example, if the well 12S is of N-type, the source diffusion layer 13S is of P-type. If the well 12S is of P-type, the source diffusion layer 13S is of N-type.

The drain diffusion layer 14S is formed over the semiconductor substrate 11S as illustrated in FIG. 2A. The drain diffusion layer 14S is formed to cover part of the well 12S in the plan view (in the Y-axis direction) as illustrated in FIG. 2A, for example. The drain diffusion layer 14S is formed to cover the right side of the well 12S (on the positive side of the X-axis), for example. The drain diffusion layer 14S is formed by implanting therein a predetermined impurity defining the characteristic of the sensor 10S. The drain diffusion layer 14S has a different conductive type from the well 12S in the N-type or P-type layer, for example. For example, if the well 12S is of N-type, the drain diffusion layer 14S is of P-type. If the well 12S is of P-type, the drain diffusion layer 14S is of N-type.

The gate insulative film 15S is formed on the well 12S, the source diffusion layer 13S, and the drain diffusion layer 14S as illustrated in FIG. 2A. The gate insulative film 15S is formed to cover the well 12S, the source diffusion layer 13S, and the drain diffusion layer 14S in the plan view (in the Y-axis direction). That is, the gate insulative film 15S electrically insulates the well 12S, the source diffusion layer 13S, and the drain diffusion layer 14S from the gate layer 16S described below. The gate insulative film 15S is made of silicon dioxide ($SiO_2$), for example.

The gate layer 16S is formed on the gate insulative film 15S as illustrated in FIG. 2A. The gate layer 16S is formed on a main surface 15Sa of the gate insulative film 15S as illustrated in FIG. 2A, for example. More specifically, the gate layer 16S is formed to cover part of the source diffusion layer 13S, part of the well 12S, and part of the drain diffusion layer 14S as illustrated in FIG. 2A, for example. Specifically, the gate layer 16S is formed to cover a region of the source diffusion layer 13S closer to the drain diffusion layer 14S (on the positive side of the X-axis), a region of the well 12S between the source diffusion layer 13S and the drain diffusion layer 14S, and a region of the drain diffusion layer 14S closer to the source diffusion layer 13S (on the negative side of the X-axis).

The gate layer 16S is configured such that an electrode support layer 16Sa made of titanium oxide ($TiO_x$), for example, and an electrode layer 16Sb made of platinum (Pt), for example, are laminated on the gate insulative film 15S in this order as illustrated in FIG. 3. Hydrogen atoms are dissociated/adsorbed on the electrode layer 16Sb. Part of hydrogen atoms ($H^+$) dissociated from the electrode layer 16Sb moves from the electrode layer 16Sb to the electrode support layer 16Sa. Part of hydrogen atoms ($H^+$) in the electrode support layer 16Sa moves to the electrode layer 16Sb.

The gate protective film 17S is formed to cover part of the gate layer 16S opposing the atmosphere and part of the gate insulative film 15S as illustrated in FIG. 2A. For example, the gate protective film 17S is formed to cover the periphery of the gate layer 16S and other than the region covered with the gate layer 16S on the gate insulative film 15S, in the plan view (in the Y-axis direction). That is, at least part of a surface of the gate layer 16S, which opposes the atmosphere, is exposed.

The well 12S, the source diffusion layer 13S, the drain diffusion layer 14S, and the gate layer 16S in the sensor 10S are made of a metal such as aluminum (Al), tungsten (W), or platinum (Pt). They are connected to the power supply unit 40, the current measurement unit 20, and the like illustrated in FIG. 1 via a wiring layer (not illustrated). A well 12R, a source diffusion layer 13R, a drain diffusion layer 14R, and a gate layer 16R in the sensor 10R are also connected to the power supply unit 40, the current measurement unit 20, and the like via a wiring layer (not illustrated).

For example, the well 12S and the source diffusion layer 13S in the sensor 10S are grounded as illustrated in FIG. 4A. The drain diffusion layer 14S is connected to a power supply 41 for applying a constant voltage VD as illustrated in FIG. 4A. The drain diffusion layer 14S is connected to the current measurement unit 20 as illustrated in FIG. 4A. The gate layer 16S is connected to a power supply 41 for applying a variable voltage as illustrated in FIG. 4A.

Figure 5A:
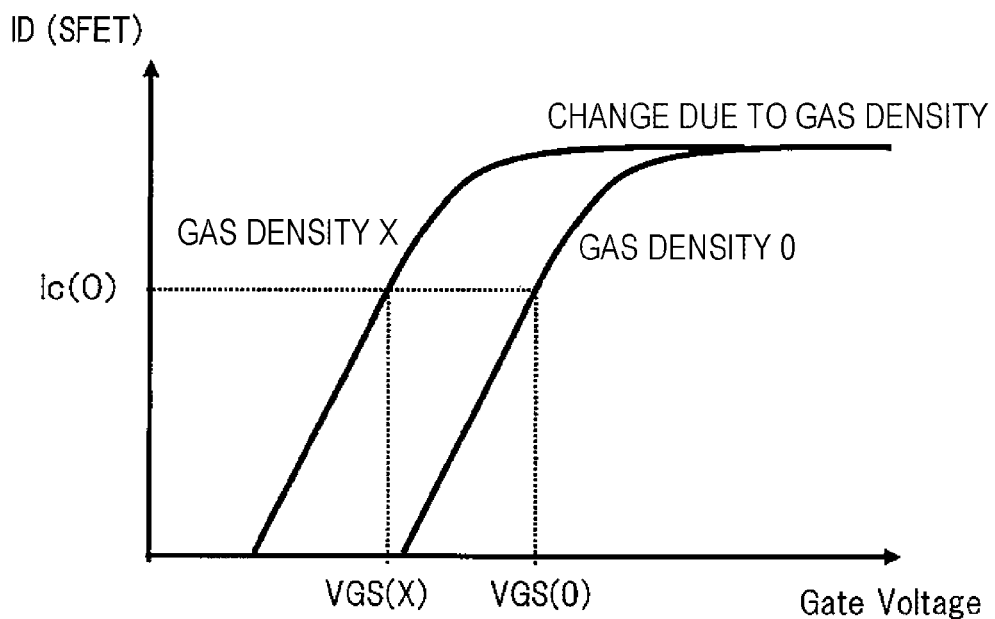
FIGS. 5A and 5B are diagrams illustrating exemplary current-voltage characteristics of the sensors according to the first embodiment of the present invention.
Figure 5B:
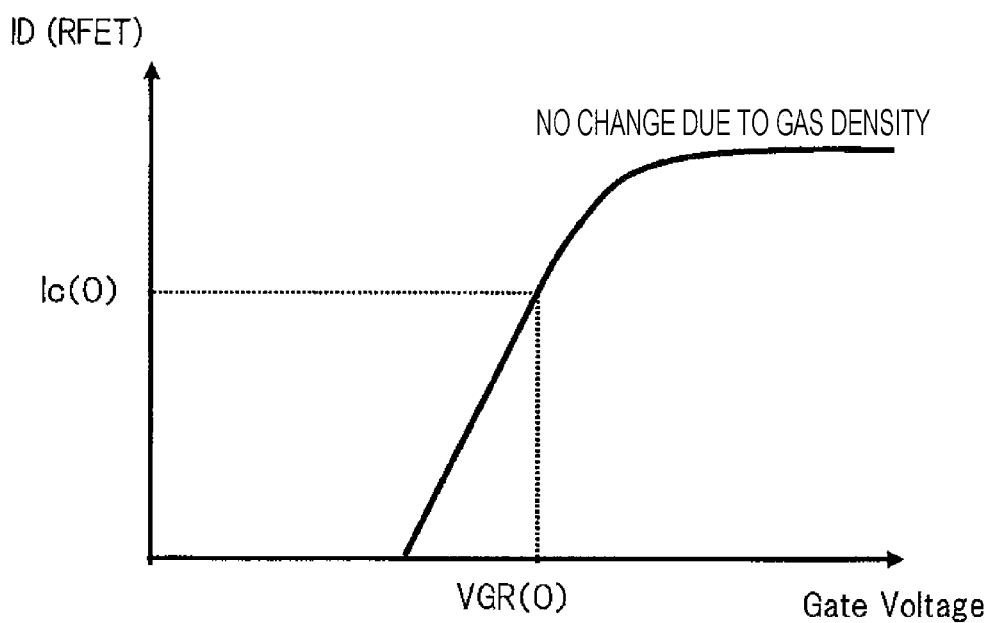

FIGS. 5A and 5B are diagrams illustrating exemplary current-voltage characteristics of the sensors according to the first embodiment of the present invention. FIG. 5A is a diagram illustrating a current-voltage characteristic of the sensor 10S. FIG. 5B is a diagram illustrating a current-voltage characteristic of the sensor 10R. When gas (such as hydrogen ions) is adsorbed on the gate layer 16S, a work function of the gate layer 16S changes. Then, as illustrated in FIG. 5A, when the gas density increases, the current-voltage characteristic of the sensor 10S moves leftward in parallel in the Figure. That is, the voltage of the gate layer 16S lowers as the gas density is higher when a threshold current (first threshold current) Ic(0) flows in the drain diffusion layer 14S.

The sensor (second FET-type sensor) 10R includes a semiconductor substrate (second semiconductor substrate) 11R, the well (second well) 12R, the source diffusion layer (second source diffusion layer) 13R, the drain diffusion layer (second drain diffusion layer) 14R, the gate insulative film (second gate insulative film) 15R, the gate layer (second gate layer) 16R, and a gate protective film 17R as illustrated in FIG. 2B.

Many components configuring the sensor 10R are similar to those configuring the sensor 10S. For example, the semiconductor substrate 11R, the well 12R, the source diffusion layer 13R, the drain diffusion layer 14R, the gate insulative film 15R, and the gate layer 16R in the sensor 10R are similar in their configurations to the semiconductor substrate 11S, the well 12S, the source diffusion layer 13S, the drain diffusion layer 14S, the gate insulative film 15S, and the gate layer 16S in the sensor 10S, respectively. Thus, a detailed description thereof will be omitted.

As illustrated in FIG. 2B, the gate protective film 17R is formed to cover an entire surface of the gate layer 16R opposing the atmosphere and the gate insulative film 15R in the plan view (in the Y-axis direction). That is, the gate layer 16R is isolated from the atmosphere.

The well 12R, the source diffusion layer 13R, the drain diffusion layer 14R, and the gate layer 16R are made of a metal such as aluminum (Al), tungsten (W), or platinum (Pt). They are connected to the power supply unit 40, the current measurement unit 20, and the like illustrated in FIG. 1 via a wiring layer (not illustrated).

For example, the well 12R and the source diffusion layer 13R are grounded as illustrated in FIG. 4B. The drain diffusion layer 14R is connected to the power supply 41 for applying a constant voltage VD as illustrated in FIG. 4B. The drain diffusion layer 14R is connected to the current measurement unit 20 as illustrated in FIG. 4B. The gate layer 16R is connected to the power supply 41 for applying a variable voltage as illustrated in FIG. 4B.

The gate layer 16R is covered with the gate protective film 17R in the sensor 10R. Thus, gas is not adsorbed on the gate layer 16R, and thus the work function of the gate layer 16R does not change. Therefore, the current-voltage characteristic of the sensor 10R does not vary depending on the gas density as illustrated in FIG. 5B.

The description will be made below assuming that the sensors 10S and 10R are of N-type FET. The sensors 10S and 10R may be of P-type, or one sensor may be of N-type and the other sensor may be of P-type.

The heater 19 is formed on a substrate such as semiconductor substrate. The heater 19 is formed of a wiring made of a metal such as aluminum (Al), tungsten (W), or platinum (Pt). The heater 19 is connected to the power supply unit 40, generates Joule heat by a voltage applied between both ends of the heater 19, and adjusts the temperature of the sensor unit 10 by the generated Joule heat. The heater 19 is grounded at one end and is connected at the other end to a power supply 41 for applying a voltage VHL as illustrated in FIG. 4C, for example. The heater 19 also functions as sensor thermometer for measuring the temperature of the sensor unit 10. At this time, the heater 19 is connected to the current measurement unit 20, for example.

The sensors 10S and 10R may be formed on different semiconductor substrates, respectively, or may be formed on the same semiconductor substrate. The heater 19 may be formed integral with the sensor 10S or the sensor 10R, or may be configured separately from them.

The current measurement unit 20 measures the currents of the sensors 10S and 10R. The current measurement unit 20 measures a source-drain current (first source-drain current) flowing between the source diffusion layer 13S and the drain diffusion layer 14S in the sensor 10S, for example. The current measurement unit 20 measures a source-drain current (second source-drain current) flowing between the source diffusion layer 13R and the drain diffusion layer 14R in the sensor 10R, for example. The current measurement unit 20 outputs the measured current data of the sensors 10S and 10R to the control unit 50 described below. The current measurement unit 20 measures the current of the heater 19.

The current measurement unit 20 outputs the measured current data of the heater 19 to the control unit 50 described below.

The gas density measurement unit 30 measures a gas density of gas to be detected in the atmosphere. For example, the gas density measurement unit 30 measures the gas density of the gas to be detected at a predetermined time on the basis of a threshold change (second threshold change) $\Delta Vg(X)$ as a difference between an inter-sensor potential difference (first inter-sensor potential difference) $VGRS(0)$ ($=VGR(0)-VGS(0)$) as a difference between a threshold voltage (third threshold voltage) $VGR(0)$ applied to the gate layer 16R when the second source-drain current is the threshold current (first threshold current) $Ic(0)$ and a threshold voltage (first threshold voltage) $VGS(0)$ applied to the gate layer 16S when the first source-drain current is the predetermined threshold current $Ic(0)$ while the gas to be detected is not present in the atmosphere, and an inter-sensor potential difference (second inter-sensor potential difference) $VGRS(X)$ ($=VGR(X)-VGS(X)$) as a difference between a threshold voltage (fourth threshold voltage) $VGR(X)$ ($=VGR(0)$) applied to the gate layer 16R when the second source-drain current is the predetermined threshold current $Ic(0)$ at the predetermined time and a threshold voltage (second threshold voltage) $VGS(X)$ applied to the gate layer 16S when the first source-drain current is the predetermined threshold current $Ic(0)$ while the gas to be detected is present in the atmosphere, and a temporal differentiation of the threshold change $\Delta Vg(X)$. The gas density measurement method will be described below in detail.

The power supply unit 40 supplies power to each unit configuring the gas sensor 1. The power supply unit 40 includes a plurality of power supplies 41 as illustrated in FIG. 1. The power supply unit 40 is configured of a power supply 41 for applying a constant voltage, a power supply 41 for applying a variable voltage, a power supply 41 for applying a periodically-varying voltage, and the like.

The number of power supplies 41 is not limited to the number (four) illustrated in FIG. 1, and may be five or more, or three or less depending on the types of applied voltages of the sensor unit 10 and the like.

The control unit 50 controls each unit configuring the gas sensor 1. The control unit 50 controls each unit to be switched ON/OFF, for example. The control unit 50 controls the power supply 41 connected to the gate layer 16S in the sensor 10S on the basis of the current data output from the current measurement unit 20. For example, the control unit 50 adjusts the voltage of the power supply 41 such that the current of the drain diffusion layer 14S in the sensor 10S is the predetermined threshold current $Ic(0)$. The control unit 50 controls the power supply 41 connected to the gate layer 16R in the sensor 10R on the basis of the current data output from the current measurement unit 20. For example, the control unit 50 adjusts the voltage of the power supply 41 such that the current of the drain diffusion layer 14R in the sensor 10R is the predetermined threshold current $Ic(0)$ at the time of measurement of the gas density.

Further, the control unit 50 measures the temperatures of the sensors 10S and 10R on the basis of the current data of the heater 19 output from the current measurement unit 20. The control unit 50 calculates a resistance value of the heater 19 on the basis of the voltage between both ends of the heater 19 and the current data of the heater 19, for example. The control unit 50 then measures the temperatures with reference to the temperature data in which the resistance value and the temperatures are associated with each other, for example. The control unit 50 controls the power supply 41 connected to the heater 19. Specifically, the control unit 50 adjusts the voltage of the power supply 41 such that the temperatures of the sensors 10S and 10R are constant at the time of measurement of the gas density.

The data I/O unit 90 inputs/outputs data to/from an external device connected to the gas sensor 1. For example, the gas sensor 1 receives various items of input data output from an external device via the data I/O unit 90. The gas sensor 1 outputs the data on the measured gas density and temperatures to an external device via the data I/O unit 90. The data I/O unit 90 may be connected to an external device in a wired manner, or may be connected to an external device in infrared communication or near field communication, for example. The data I/O unit 90 may be connected to an external device via a network.

<Gas Density Measurement Method>

A gas density measurement method using the gas sensor according to the present embodiment will be described below. The description will be made below assuming that a gas density of hydrogen gas as exemplary gas to be detected is measured.

At first, the control unit 50 adjusts the temperature of the sensor unit 10. For example, the control unit 50 turns on the power supply 41 connected to the heater 19 thereby to apply a voltage between both ends of the heater 19.

The control unit 50 then turns on the power supplies 41 connected to the units in the sensors 10S and 10R. The power supplies 41 then apply a predetermined voltage to each unit in the sensors 10S and 10R. For example, the power supply 41 connected to the well 12S and the source diffusion layer 13S in the sensor 10S applies a voltage of 0 V. The power supply 41 connected to the gate layer 16S in the sensor 10S applies the predetermined threshold voltage $VGS(0)$ such that the first source-drain current is the threshold current $Ic(0)$. The power supply 41 connected to the well 12R and the source diffusion layer 13R in the sensor 10R applies a voltage of 0 V. The power supply 41 connected to the drain diffusion layer 14R applies the voltage VD. The power supply 41 connected to the gate layer 16R in the sensor 10R applies the predetermined threshold voltage $VGR(0)$ such that the second source-drain current is the threshold current $Ic(0)$.

The threshold voltages $VGS(0)$ and $VGR(0)$ of the sensors 10S and 10R may be previously measured at a gas density of 0. The control unit 50 may read the data on the previously-measured threshold voltages $VGS(0)$ and $VGR(0)$ from a data storage unit (not illustrated) as needed, for example. The control unit 50 outputs the data on the threshold voltages $VGS(0)$ and $VGR(0)$ to the gas density measurement unit 30, for example.

The control unit 50 then measures the threshold voltages $VGS(X)$ and $VGR(X)$ of the sensors 10S and 10R when the hydrogen gas is contained in the atmosphere. The control unit 50 adjusts the voltages of the power supplies 41 connected to the gate layers 16S and 16R with reference to the current data output from the current measurement unit 20 thereby to measure the threshold voltages $VGS(X)$ and $VGR(X)$, for example. The gate layer 16R in the sensor 10R is isolated from the atmosphere by the gate protective film 17R, and thus the threshold voltage $VGR(X)$ of the sensor 10R is the same as the threshold voltage $VGR(0)$ at a gas density of 0. The control unit 50 outputs the data on the measured threshold voltages $VGS(X)$ and $VGR(X)$ to the gas density measurement unit 30, for example.

The gas density measurement unit 30 then calculates a threshold change of the sensor 10S on the basis of the threshold voltages $VGS(0)$ and $VGR(0)$ and the threshold voltages VGS (X) and VGR(X) output from the control unit 50. For example, the gas density measurement unit 30 calculates the threshold change of the sensor 10S on the basis of a difference between the inter-sensor potential difference VGRS(0) when the hydrogen gas is not present in the atmosphere and the inter-sensor potential difference VGRS(X) when the hydrogen gas is present in the atmosphere. That is, the threshold change $\Delta Vg(X)$ of the sensor 10S is expressed as follows.

$$\Delta Vg(X)=VGRS(0)-VGRS(X) \quad \text{(Equation 1)}$$

The threshold voltages VGR(0) and VGR(X) of the sensor 10R are considered in the threshold change expressed in (Equation 1). This is for restricting an effect of noise caused in the sensor unit 10, such as change in temperature.

When a variation in the threshold voltage VGS due to noise is small, the gas density measurement unit 30 may measure the gas density by only the sensor 10S. In this case, the gas density measurement unit 30 measures the gas density of the hydrogen gas at a predetermined time on the basis of a threshold change (first threshold change) Vg(X) as a difference between the threshold voltage (first threshold voltage) VGS(0) applied to the gate layer 16S when the first source-drain current is the predetermined threshold current Ic(0) while the hydrogen gas is not present in the atmosphere and the threshold voltage (second threshold voltage) VGS(X) applied to the gate layer 16S when the first source-drain current is the predetermined threshold current Ic(0) at the predetermined time while the hydrogen gas is present in the atmosphere, and a temporal differentiation of the threshold change Vg(X). Thus, the threshold change $\Delta Vg(X)$ in this case is expressed as follows.

$$\Delta Vg(X)=VGS(0)-VGS(X) \quad \text{(Equation 2)}$$

The Langmuir dissociation/adsorption process at the time of a chemical reaction between the gate layer 16S and the hydrogen gas in a non-equilibrium state will be considered below. A rate of the hydrogen adsorption site occupied by hydrogen relative to the entire hydrogen adsorption site is assumed as occupancy $\theta$ ($0 \le \theta \le 1$) in the gate layer 16S in the sensor 10S. An adsorption phenomenon and a desorption phenomenon are always occurring in the hydrogen adsorption site whether in the equilibrium state or in the non-equilibrium state. An adsorption speed and a desorption speed of the hydrogen gas are equal to each other in the equilibrium state. On the other hand, the adsorption speed and the desorption speed of the hydrogen gas are different from each other in the non-equilibrium state. The adsorption speed V1 and the desorption speed V2 of the hydrogen gas are expressed by use of the occupancy $\theta$ and the hydrogen gas density X as follows.

$$V1=k1\times(1-\theta)^2\times X \quad \text{(Equation 3)}$$

$$V2=k2\times\theta^2 \quad \text{(Equation 4)}$$

Where k1 and k2 are parameters depending on the temperature at the time of measurement of the gas density, the material and quality of the gate layer 16S, and the like. The temporal differentiation $d\theta/dt$ of the occupancy $\theta$ is expressed by use of (Equation 3) and (Equation 4) as follows.

$$d\theta/dt=V1-V2=k1\times(1-\theta)^2\times X-k2\times\theta^2 \quad \text{(Equation 5)}$$

The hydrogen gas density X is expressed in the following Langmuir equation based on (Equation 5).

$$X=[d\theta/dt+k2\times\theta^2]/[k1\times(1-\theta)^2] \quad \text{(Equation 6)}$$

[Considerations of Threshold Change Rate-determining Process Relative to Change in Gas Eensity]

Figure 6A:
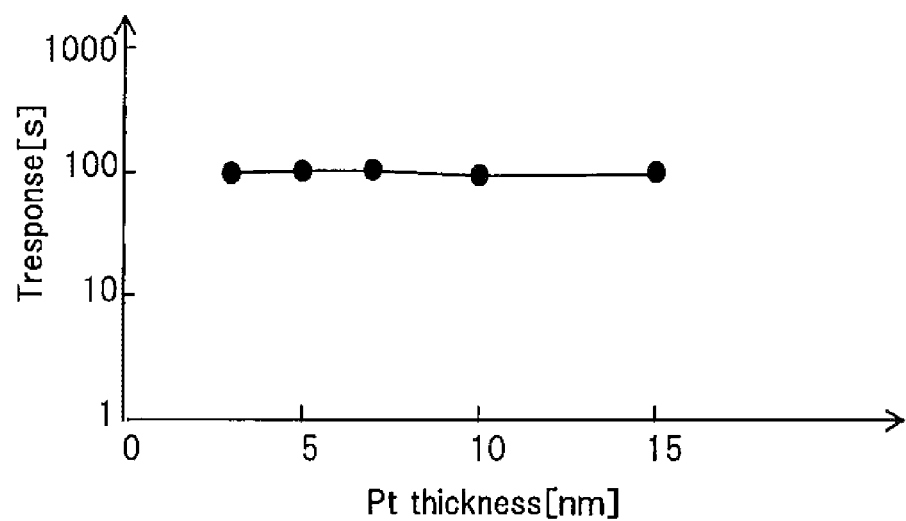
FIGS. 6A and 6B are diagrams illustrating relationships between a configuration of a gate layer and a response time according to the first embodiment of the present invention.
Figure 6B:
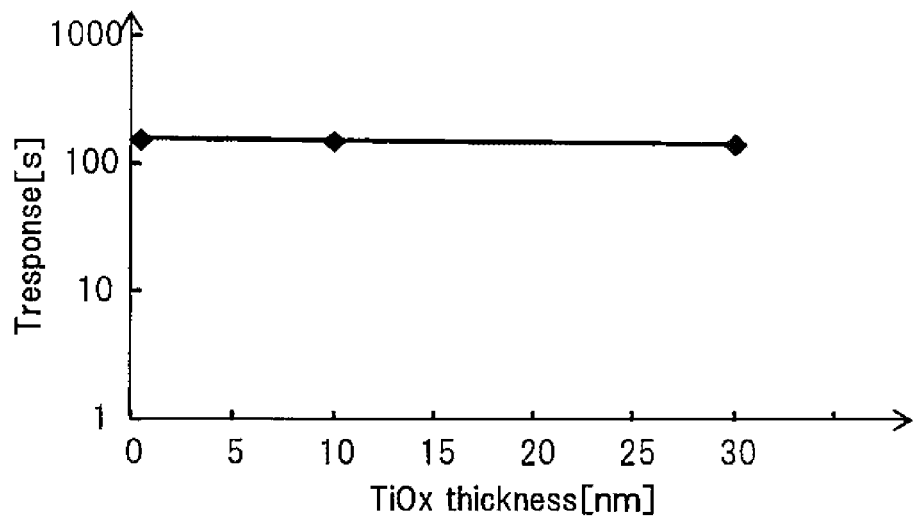
Figure 7:
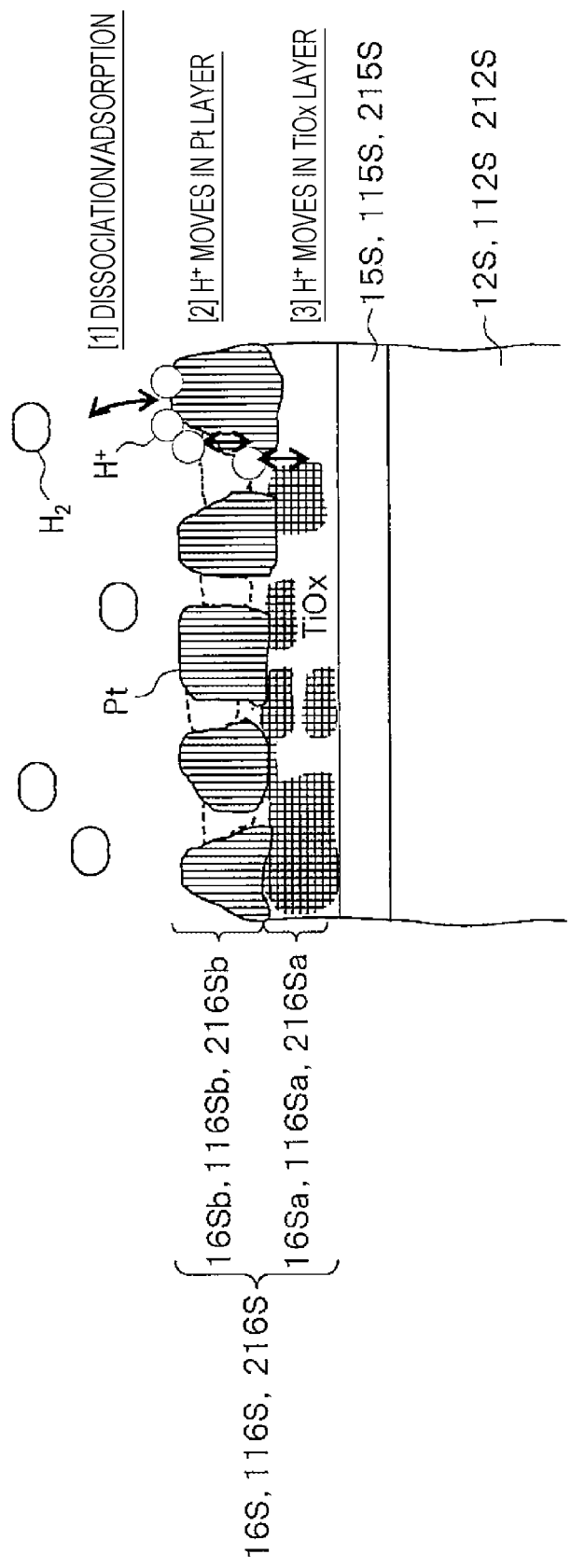
FIG. 7 is a diagram illustrating how the gate layer reacts with hydrogen gas according to the first embodiment of the present invention.

A relationship between the hydrogen gas density X and the threshold change $\Delta Vg(X)$ of the sensor 10S will be described herein. FIGS. 6A and 6B are diagrams illustrating the relationships between a configuration of the gate layer and a response time according to the first embodiment of the present invention. FIG. 6A is a diagram illustrating a relationship between a response time of the threshold change $\Delta Vg(X)$ to a change in the gas density X and a thickness of the electrode layer 16Sb of the gate layer 16S. FIG. 6B is a diagram illustrating a relationship between a response time of the threshold change $\Delta Vg(X)$ to a change in the gas density X and a thickness of the electrode support layer 16Sa of the gate layer 16S. FIG. 7 is a diagram illustrating how the gate layer reacts with the hydrogen gas according to the first embodiment of the present invention. The response time of the threshold change $\Delta Vg(X)$ rarely depends on the thickness of the electrode layer 16Sb as illustrated in FIG. 6A. Further, the response time of the threshold change $\Delta Vg(X)$ rarely depends on the thickness of the electrode support layer 16Sa as illustrated in FIG. 6B.

A rate-determining process of the temporal change in the threshold change $\Delta Vg(X)$ relative to the change in the hydrogen gas density X will be considered. It is assumed that [1] the hydrogen gas ($H_2$) dissociation/adsorption process in the electrode layer 16Sb, [2] the hydrogen gas ($H^+$) moving process in the electrode layer 16Sb, and [3] the hydrogen gas ($H^+$) moving process in the electrode support layer 16Sa are performed in the gate layer 16S as illustrated in FIG. 7, for example. When the processes [1] to [3] are compared with FIGS. 6A and 6B, it can be seen that the processes [2] and [3] rarely give an effect on the response time of the threshold change $\Delta Vg(X)$. This means that when the occupancy $\theta$ of the hydrogen adsorption site in the gate layer 16S changes, the processes [2] and [3] are quickly performed and the change in the occupancy $\theta$ is rapidly reflected on the threshold change $\Delta Vg(X)$. The result assumes that the occupancy $\theta$ of the hydrogen adsorption site in the gate layer 16S and the threshold change $\Delta Vg(X)$ are in a proportional relationship even in the non-equilibrium state similarly as in the equilibrium state.

[Measurement of Gas Density]

Thus, the threshold change $\Delta Vg(X)$ is expressed as in the following equation assuming the value of the threshold change $\Delta Vg(X)$ in a state ($\theta=1$) in which the entire hydrogen adsorption site in the gate layer 16S is occupied with the hydrogen gas as a parameter $\Delta Vgmax$.

$$\Delta Vg(X)=\theta\times\Delta Vgmax \quad \text{(Equation 7)}$$

The hydrogen gas density X is expressed by use of the threshold change $\Delta Vg(X)$ and the temporal differentiation $d\Delta Vg(X)/dt$ of the threshold change as follows on the basis of (Equation 6) and (Equation 7).

$$X=[\Delta Vgmax\times(d\Delta Vg(X)/dt)+k2\times(\Delta Vg(X))^2]/[k1\times(\Delta Vgmax-\Delta Vg(X))^2] \quad \text{(Equation 8)}$$

where $\Delta Vgmax$ is a parameter depending on the temperature at the time of measurement of the gas density, the material and quality of the gate layer 16S, and the like.

Therefore, the gas density measurement unit 30 measures the threshold change $\Delta Vg(X)$ and the temporal differentiation $d\Delta Vg(X)/dt$ of the threshold change, and calculates the hydrogen gas density X on the basis of (Equation 8).

The gas density measurement unit 30 measures the gas density of the gas to be detected at a predetermined interval. For example, the gas density measurement unit 30 acquires a temporal change in the threshold change $\Delta Vg(X)$ at a shorter interval than a temporal scale of the change in the hydrogen density in the atmosphere. Therefore, the gas density measurement unit 30 measures the gas density at an interval of 0.1 seconds or less, for example. Thereby, the response time of the gas sensor can be reduced even in the gas sensor using FET-type sensors. The gas density measurement unit 30 starts measuring the gas density within one second, for example, after the gas sensor is activated.

Effects of Present Embodiment

According to the present embodiment, the gas density measurement unit 30 measures the gas density of the gas to be detected on the basis of the threshold change $\Delta Vg(X)$ calculated from the threshold voltages VGS(0), VGS(X), VGR(0), and VGR(X) in the sensors 10S and 10R, and the temporal differentiation $d\Delta Vg(X)/dt$ of the threshold change. With the configuration, the gas density is measured while a chemical reaction with the gas to be detected in the sensor 10S is in the non-equilibrium state, and thus the gas density is measured in a short time.

Further, according to the present embodiment, the gas density is measured on the basis of the Langmuir equation in (Equation 8), for example. With the configuration, the parameters and index are appropriately selected depending on circumstances, thereby accurately measuring the gas density of the gas to be detected. Further, with the configuration, an effect of noise caused in the sensor unit 10 can be restricted, thereby accurately measuring the gas density even under circumstances with many noises.

According to the present embodiment, the Langmuir equation is derived assuming that the occupancy of the gas to be detected in the adsorption site in the gate layer 16S is proportional to the threshold change $\Delta Vg(X)$. With the configuration, the Langmuir equation is expressed in a simple form, which facilitates measurement of the gas density. Loads on the gas density measurement unit 30 at the time of measurement of the gas density are alleviated. Thereby, a time required to measure the gas density is shortened.

According to the present embodiment, the gas density measurement unit 30 sets an index n in the Langmuir equation depending on the kind of the gas to be detected. With the configuration, the gas densities of different kinds of gas depending on circumstances can be measured.

According to the present embodiment, the gate layer 16S is configured such that the electrode support layer 16Sa made of titanium oxide and the electrode layer 16Sb made of platinum are laminated, and the gas density measurement unit 30 sets the index in the Langmuir equation depending on the number of hydrogen atoms in the molecules of the gas to be detected. With the configuration, the Langmuir equation depending on the kind of the gas to be detected is used, thereby accurately measuring the gas density of the gas containing hydrogen atoms.

According to the present embodiment, the gas density measurement unit 30 sets the index in the Langmuir equation at 2 and measures the gas density of the hydrogen gas. With the configuration, the Langmuir equation according to the hydrogen gas is used, and thus the gas density of the hydrogen gas can be accurately measured.

According to the present embodiment, the sensor unit 10 includes the heater 19. With the configuration, the gas density is measured while the sensor unit 10 is set at a predetermined temperature, and thus the gas density can be measured more accurately.

The heater 19 is adjusted in the amount of generated heat depending on the temperature of the atmosphere. With the configuration, a change in temperature of the sensor unit 10 can be restricted even when the temperature of the atmosphere changes, and thus the gas density can be accurately measured.

According to the present embodiment, the gas density can be measured by only the sensor 10S under circumstances with low impact of noise. With the configuration, the configuration of the sensor unit 10 is simplified, and thus the sensor unit 10 is downsized. Thereby, the gas sensor 1 is downsized.

According to the present embodiment, the gas density measurement unit 30 measures the gas density of the gas to be detected at a predetermined interval. With the configuration, the gas density is continuously measured at the predetermined interval, and thus a change in the gas density is detected.

According to the present embodiment, the gas density measurement unit 30 measures the gas density at an interval of 0.1 seconds or less. With the configuration, the gas density is measured in a short time, and thus a change in the gas density is immediately detected.

<Gas Density Measurement Method in Equilibrium State>

The gas density measurement method in the equilibrium state will be described herein. A chemical reaction in the sensor eventually enters the equilibrium state. Then, the threshold change $\Delta Vg(X)$ converges to a predetermined value depending on the gas density X. According to JP 2016-85124 A, a relationship expressed below lies between the gas density X and the converged threshold change $\Delta Vg(X)$ according to the Langmuir dissociation/adsorption.

$$\Delta Vg(X) = \Delta Vg\max \times [(X/X0)^{0.5}/(1+(X/X0)^{0.5})] \quad \text{(Equation 9)}$$

where X0 indicates the gas density when the threshold change $\Delta Vg(X)$ is ½ of $\Delta Vg\max$.

Figure 8:
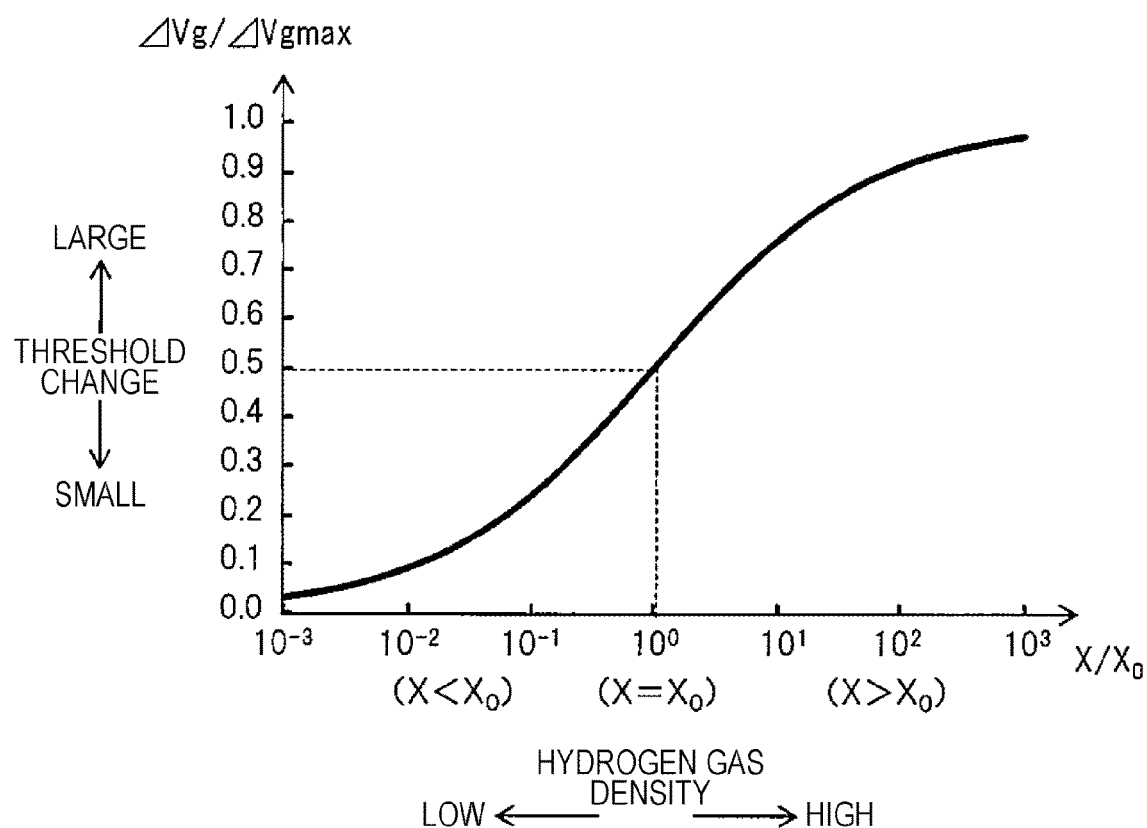
FIG. 8 is a diagram illustrating an exemplary relationship between threshold change and gas density in an equilibrium state.
Figure 9A:
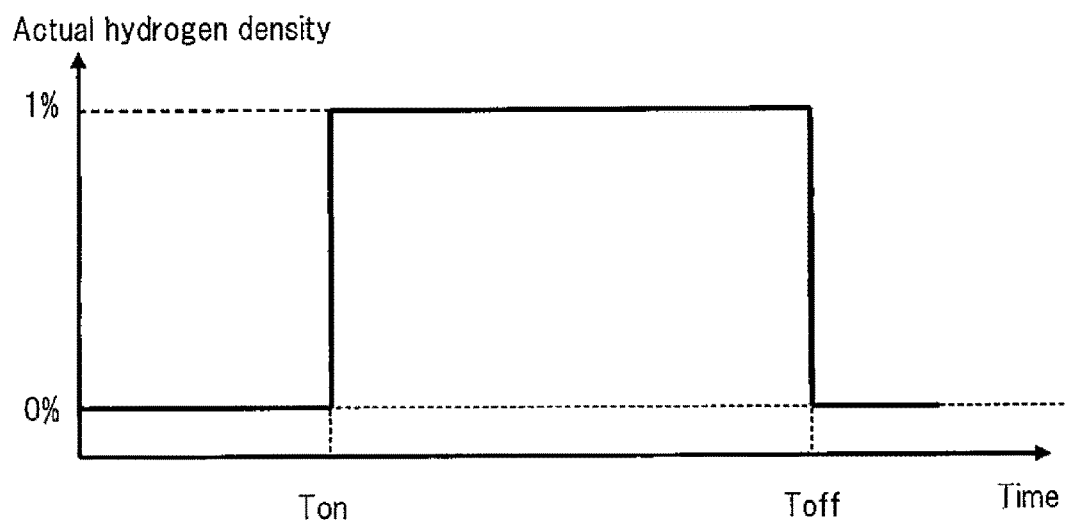
FIGS. 9A and 9B are diagrams illustrating response characteristics relative to a change in gas density in an equilibrium state.
Figure 9B:
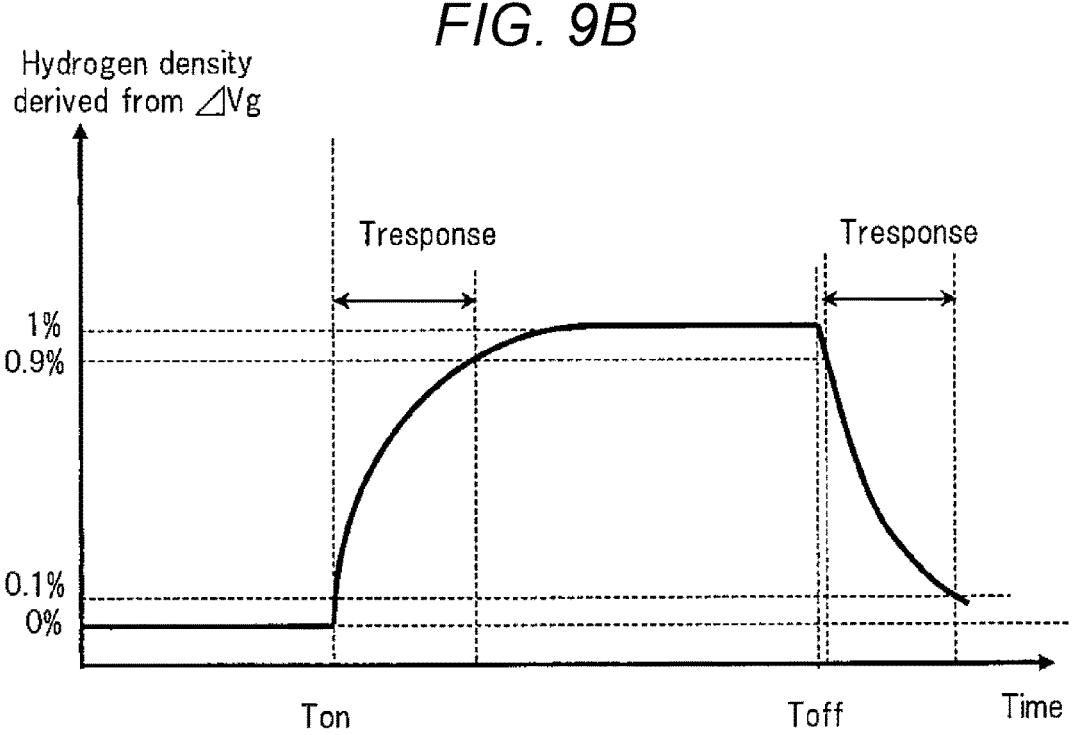

FIG. 8 is a diagram illustrating an exemplary relationship between threshold change and gas density in the equilibrium state. FIGS. 9A and 9B are diagrams illustrating the response characteristics relative to a change in the gas density in the equilibrium state. FIG. 9A illustrates a temporal change in the hydrogen gas density in the atmosphere supplied from a test device to the gas sensor. FIG. 9B illustrates a temporal change in the hydrogen gas density converted and measured by the relationship of FIG. 8 on the basis of the threshold change $\Delta Vg(X)$ measured by the gas sensor.

The hydrogen gas density in the atmosphere changes from 0% to 1% at time Ton as illustrated in FIG. 9A. On the other hand, the converted hydrogen gas density starts increasing at time Ton as illustrated in FIG. 9B. Thereafter, the converted gas density converges to 1% while keeping gently increasing as illustrated in FIG. 9B. The hydrogen gas density in the atmosphere changes from 1% to 0% at time Toff as illustrated in FIG. 9A. On the other hand, the converted gas density starts decreasing at time Toff as illustrated in FIG. 9B. Thereafter, the converted gas density converges to 0% while keeping gently decreasing as illustrated in FIG. 9B.

Tresponse takes from several seconds to several hundred seconds or more assuming a time for which the converted gas density increases from 10% (or a hydrogen gas density of 0.1%) of the actual hydrogen gas density to 90% (or a hydrogen gas density of 0.9%) as response speed Tresponse of the gas sensor when the hydrogen gas density increases. Tresponse takes from several seconds to several hundred seconds or more assuming a time for which the converted gas density decreases from 90% (or a hydrogen gas density of 0.9%) of the actual hydrogen gas density to 10% (or a hydrogen gas density of 0.1%) as response speed Tresponse of the gas sensor when the hydrogen gas density decreases. Therefore, the response time is longer in FET-type sensors than contact burning-type sensors or gas heat conduction-type sensors.

<Comparison of Hydrogen Gas Density Measurement Results>

Figure 10A:
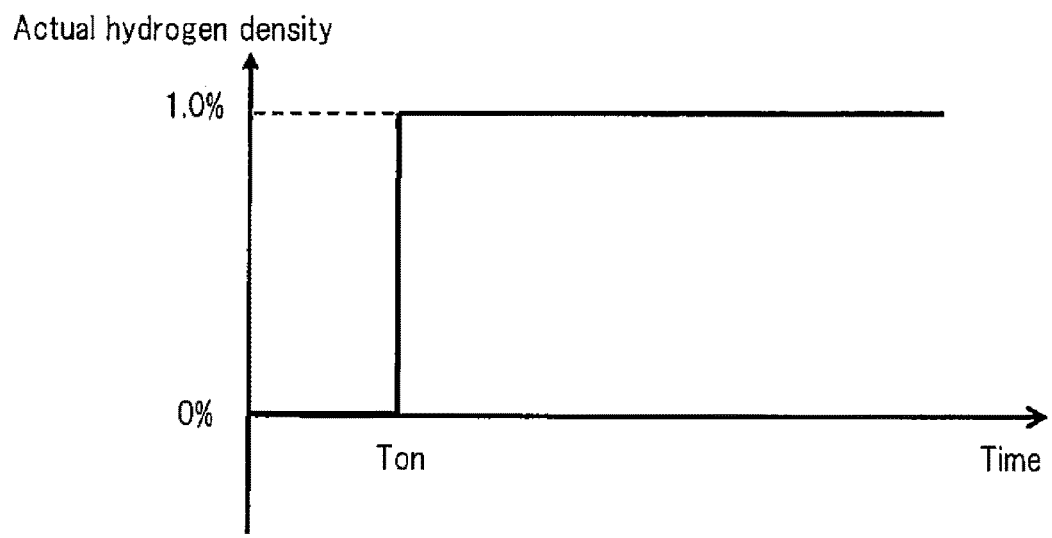
FIGS. 10A and 10B are diagrams illustrating exemplary gas density measurement results according to the first embodiment of the present invention.
Figure 10B:
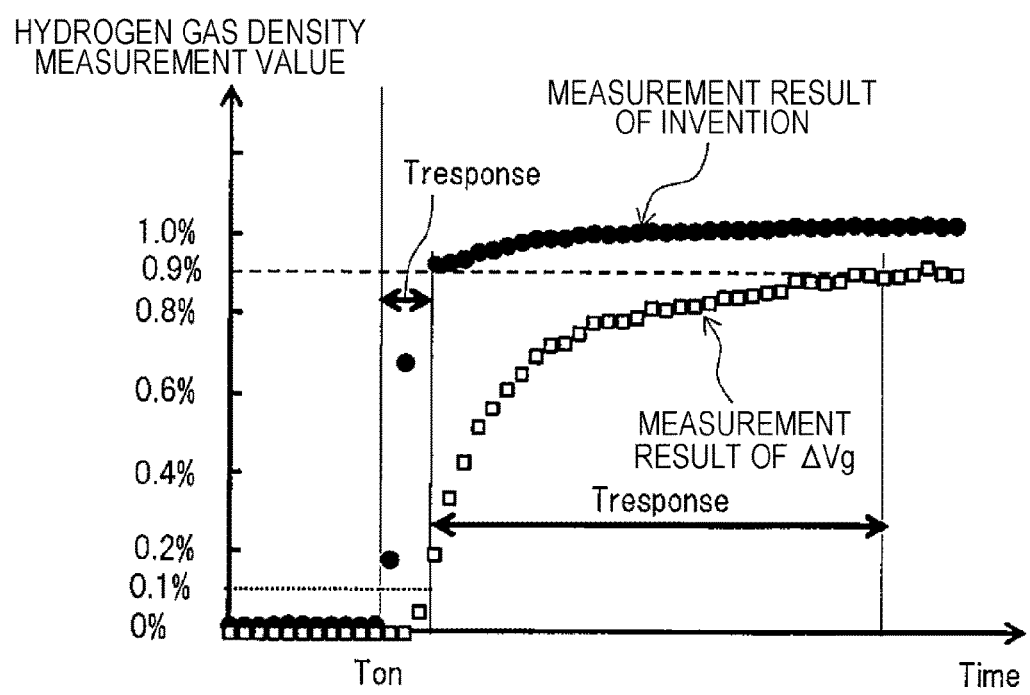

The gas density measurement results using (Equation 8) will be described herein. FIGS. 10A and 10B are diagrams illustrating exemplary gas density measurement results according to the first embodiment of the present invention. FIG. 10A is a diagram illustrating a temporal change of the actual hydrogen gas density in the atmosphere. FIG. 10B is a diagram in which the hydrogen gas density measured by use of (Equation 8) and the hydrogen gas density measured by use of (Equation 9) by the gas density measurement unit 30 are overlapped. Herein, the hydrogen gas density measurement results are illustrated when the actual hydrogen gas density in the atmosphere instantaneously increases from 0% to 1.0% at time Ton as illustrated in FIG. 10A.

At first, the hydrogen gas density measured by use of (Equation 9) increases slightly after time Ton as illustrated in FIG. 10B. The hydrogen gas density gently increases up to about 0.9% as illustrated in FIG. 10B. In this way, the hydrogen gas density measured by use of (Equation 9) has a long response time relative to the change in the gas density.

To the contrary, the hydrogen gas density measured by use of (Equation 8) increases up to about 0.9% in a short time from time Ton. Thereafter, the hydrogen gas density increases up to 1.0%. In this way, the hydrogen gas density measured by use of (Equation 8) has a short response time relative to the change in the gas density.

Second Embodiment

Figure 11:
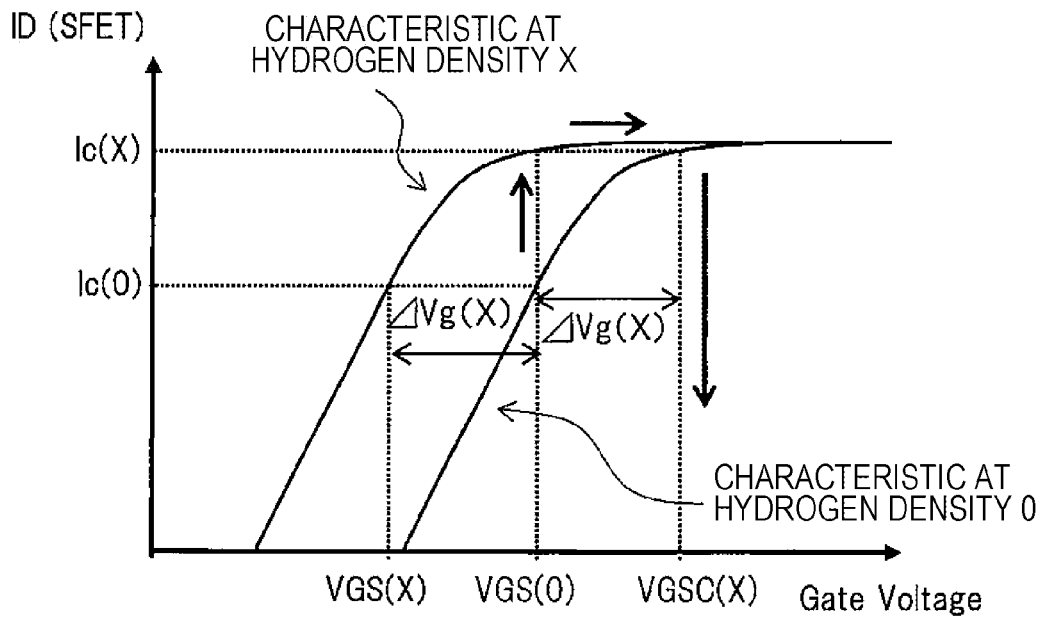
FIG. 11 is a diagram for explaining a gas density measurement method according to a second embodiment of the present invention.

A second embodiment of the present invention will be described below. A gas sensor for measuring a gas density in a different method from the above embodiment will be described according to the present embodiment. The description of the parts common with the above embodiment will be basically omitted below. FIG. 11 is a diagram for explaining a gas density measurement method according to the second embodiment of the present invention.

According to the present embodiment, the current measurement unit 20 measures a predetermined current Ic(X) for the first source-drain current when the threshold voltage VGS(0) is applied to the gate layer 16S while the gas to be detected is present in the atmosphere. The gas density measurement unit 30 detects a predetermined voltage VGSC(X) applied to the gate layer 16S when the first source-drain current is the predetermined current Ic(X) while the gas to be detected is not present in the atmosphere, and calculates the threshold change ΔVg(X) on the basis of the predetermined voltage VGSC(X) and the threshold voltage VGS(0).

For example, when the gas sensor 1 is activated, the threshold voltage VGS(0) is applied to the gate layer 16S. The voltage of the gate layer 16S is kept at the threshold voltage VGS(0) also after the gas density starts being measured.

In the meanwhile, the current measurement unit 20 measures the source-drain current of the sensor 10S, and outputs the current data on the measured current value to the gas density measurement unit 30 via the control unit 50.

The gas density measurement unit 30 then acquires the information on the current Ic(X) at a gas density of X on the basis of the current data output from the current measurement unit 20. The gas density measurement unit 30 then detects the voltage VGSC(X) of the gate layer 16S with the current Ic(X) at a gas density of 0 on the basis of the voltage-current characteristic illustrated in FIG. 11 via the control unit 50.

The gas density measurement unit 30 then calculates the threshold change ΔVg(X) at a gas density of X on the basis of a difference between the voltage VGCS(X) and the threshold voltage VGS(0). That is, the threshold change ΔVg(X) according to the present embodiment is expressed as follows.

$$\Delta Vg(X) = VGSC(X) - VGS(0) \qquad \text{(Equation 10)}$$

The thus-calculated threshold change matches with the threshold change calculated in the method according to the first embodiment. The gas density measurement unit 30 then calculates the gas density X on the basis of (Equation 8) and (Equation 10).

The following effects according to the present embodiment can be obtained in addition to the effects according to the above embodiment. According to the present embodiment, the gas density measurement unit 30 calculates the threshold change ΔVg(X) by measuring the source-drain current when the voltage applied to the gate layer 16S in the sensor 10S is kept at the threshold voltage VGS(0). With the configuration, the voltage applied to the gate layer 16S does not need to be changed while the gas density is being measured, thereby alleviating loads on the gas density measurement.

Third Embodiment

Figure 12:
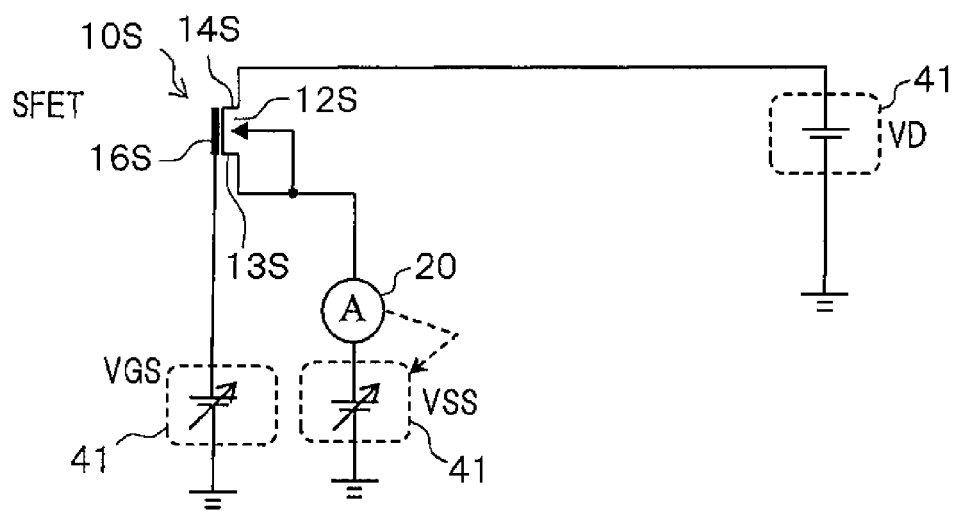
FIG. 12 is a diagram illustrating an exemplary connection configuration in the sensor unit according to a third embodiment of the present invention.
Figure 13:
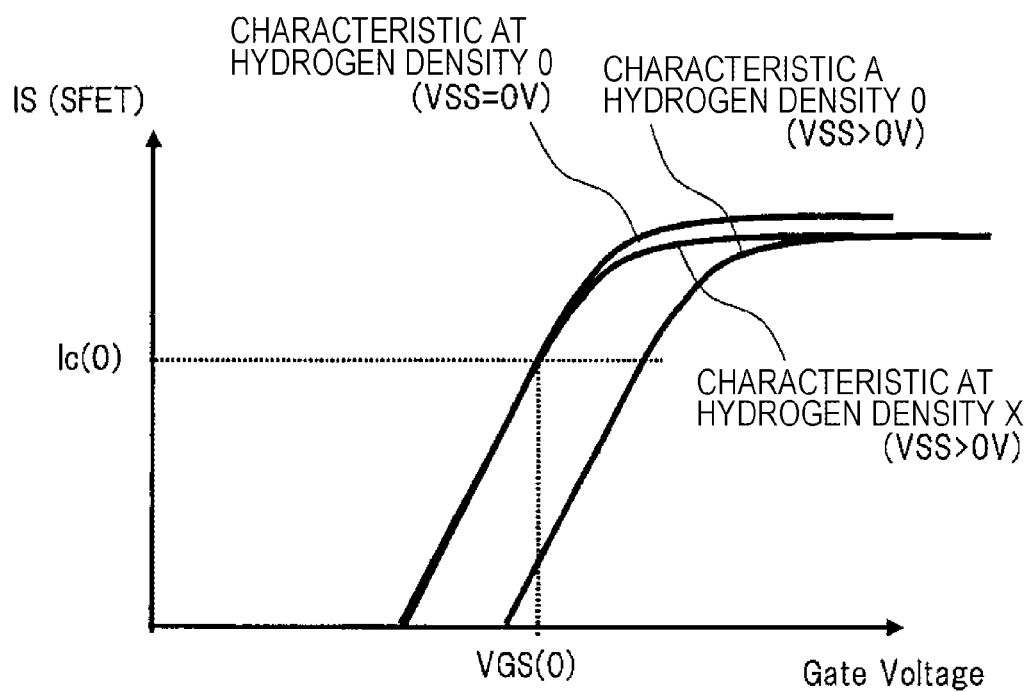
FIG. 13 is a diagram illustrating an exemplary current-voltage characteristic of a sensor according to the third embodiment of the present invention.

A third embodiment of the present invention will be described below. A gas density measurement method in a different way from the above embodiments will be described according to the present embodiment. The description of the parts common with the above embodiments will be basically omitted below. FIG. 12 is a diagram illustrating an exemplary connection configuration in the sensor unit according to the third embodiment of the present invention. FIG. 13 is a diagram illustrating exemplary current-voltage characteristics of a sensor according to the third embodiment of the present invention. FIG. 13 illustrates the current (first source-drain current)-gate voltage characteristics when a voltage VSS of the well 12S and the source diffusion layer 13S changes. FIG. 13 illustrates a current-gate voltage characteristic when the gas density is 0 and the voltage of the well 12S and the source diffusion layer 13S is 0 V (VSS=0 V). FIG. 13 illustrates a current-gate voltage characteristic when the gas density is 0 or X and the voltage of the well 12S and the source diffusion layer 13S is higher than 0 V (VSS>0 V).

The well 12S and the source diffusion layer 13S are connected with the power supply 41 for applying the variable voltage VSS as illustrated in FIG. 12.

The threshold voltage VGS(0) is applied to the gate layer 16S according to the present embodiment. The gas density measurement unit 30 calculates the threshold change ΔVg (X) on the basis of a first well voltage VSS1 applied to the well 12S when the first source-drain current is the predetermined threshold current Ic(0) while the gas to be detected is not present in the atmosphere and a second well voltage VSS2 applied to the well 12S when the first source-drain current is the predetermined threshold current Ic(0) at a predetermined time while the gas to be detected is present in the atmosphere.

For example, when the gas sensor 1 is activated, the threshold voltage VGS(0) is applied to the gate layer 16S. The power supply 41 connected to the well 12S and the source diffusion layer 13S applies the variable voltage VSS. In the meanwhile, the current measurement unit 20 measures the source-drain current of the sensor 10S, and outputs the current data on the measured current value to the gas density measurement unit 30 via the control unit 50. The voltage of the power supply 41 is adjusted on the basis of the current data such that the first source-drain current is the threshold current Ic(0).

The control unit 50 measures the voltage (first well voltage) VSS1 of the well 12S at a gas density of 0 and the voltage (second well voltage) VSS2 of the well 12S at a gas density of X. The control unit 50 outputs the information on the measured first well voltage VSS1 and second well voltage VSS2 to the gas density measurement unit 30.

The gas density measurement unit 30 calculates the threshold change ΔVg(X) on the basis of the measured first well voltage VSS1 and second well voltage VSS2. For example, the gas density measurement unit 30 calculates the threshold change ΔVg(X) in the following equation.

$$\Delta Vg(X) = VSS2 - VSS1$$

For example, the threshold change ΔVg(X)=VSS is established at the first well voltage VSS1=0 and the second well voltage VSS2=VSS.

The waveform of the current-gate voltage characteristic of the sensor 10S moves in the positive direction of the gate voltage (rightward in the Figure) as illustrated in FIG. 13 when the voltage of the well 12S and the source diffusion layer 13S changes from 0 to positive (Vss>0) at a gas density of 0. The movement of the waveform is not parallel unlike FIG. 11 but involves a change in the waveform, for example. The change in the waveform is caused since the voltage between the source diffusion layer 13S and the drain diffusion layer 14S changes depending on the gas density. As illustrated in FIG. 13, the waveform largely changes as the first source-drain current is higher. Thus, it is desirable that an appropriate value is selected for the threshold current Ic(0) such that an effect of the change in the waveform is restricted at the time of measurement of the gas density.

On the other hand, when the hydrogen density changes from to X while the voltage applied to the well 12S is kept constant, the waveform of the current-gate voltage characteristic moves in parallel in the negative direction of the gate voltage (leftward in the Figure) as illustrated in FIG. 13. This is similar to FIG. 5, for example.

A constant voltage may be applied to one of the source diffusion layer 13S and the well 12S and a variable voltage may be applied to the other of them. In this case, the waveform of the current-gate voltage characteristic largely changes. Thus, it is desirable that the data on the voltages applied to the gate layer 16S, the source diffusion layer 13S, and the well 12S when the first source-drain current is the threshold current Ic(0) at a gas density of 0 is previously acquired to generate a database.

The following effects according to the present embodiment can be obtained in addition to the effects according to the above embodiments. According to the present embodiment, the gas density measurement unit 30 keeps the voltage applied to the gate layer 16S in the sensor 10S at the threshold voltage VGS(0), and calculates the threshold change ΔVg(X) on the basis of the voltage applied to the well 12S when the first source-drain current is the threshold current Ic(0). With the configuration, the gas density is measured without changing the voltage applied to the gate layer 16S.

Fourth Embodiment

A fourth embodiment of the present invention will be described below. The description of the parts common with the above embodiments will be basically omitted below. A gas sensor using capacitors for the sensor unit will be described according to the present embodiment.

Figure 14A:
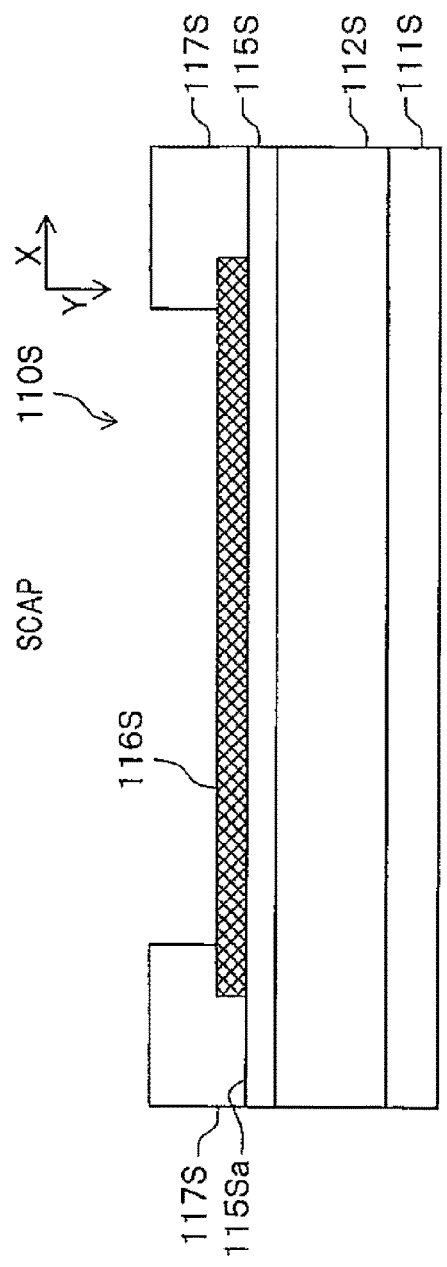
FIGS. 14A and 14B are cross-section views illustrating exemplary configurations in a sensor unit according to a fourth embodiment of the present invention.
Figure 14B:
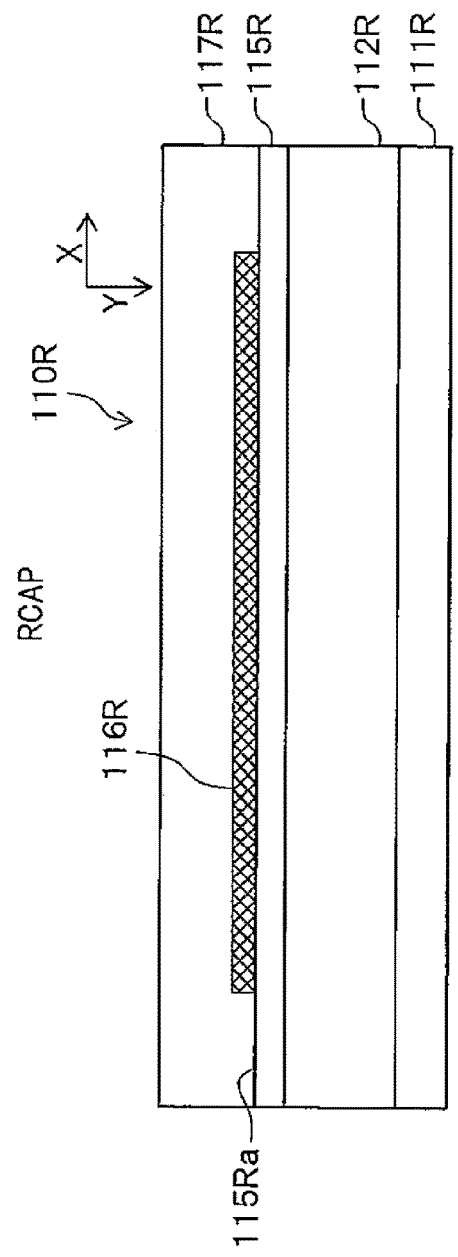
Figure 15A:
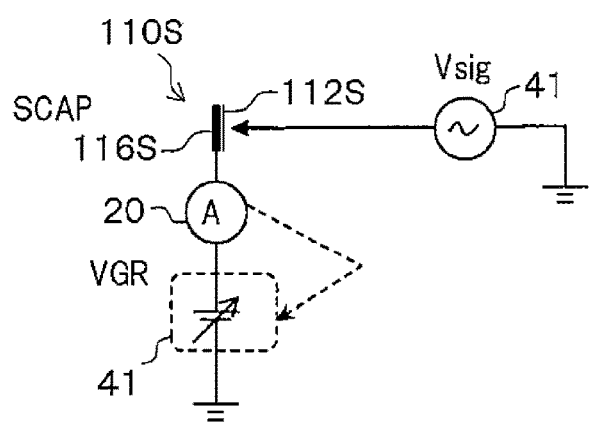
FIGS. 15A to 15C are diagrams illustrating exemplary connection configurations in the sensor unit according to the fourth embodiment of the present invention.
Figure 15B:
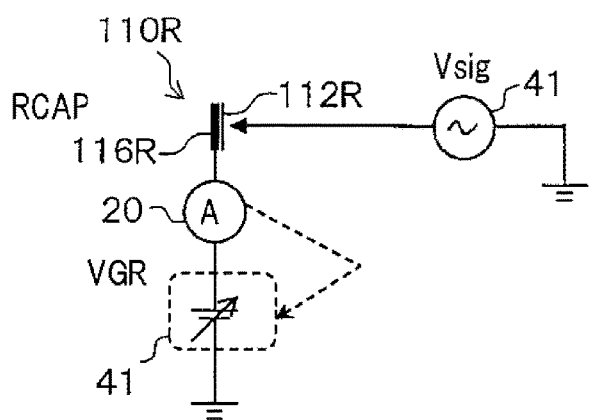
Figure 15C:
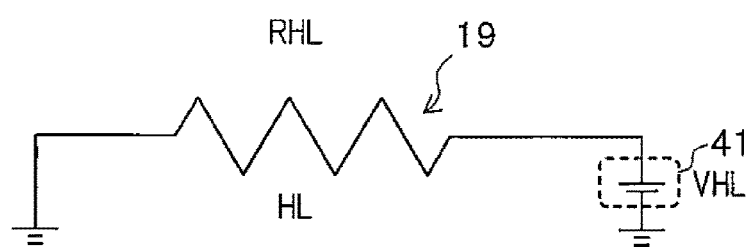

FIGS. 14A and 14B are cross-section views illustrating exemplary configurations in a sensor unit according to the fourth embodiment of the present invention. FIG. 14A is a cross-section view of a sensor 110S and FIG. 14B is a cross-section view of a sensor 110R. FIGS. 15A to 15C are diagrams illustrating exemplary connection configurations in the sensor unit according to the fourth embodiment of the present invention. FIG. 15A is a diagram illustrating an exemplary connection configuration of the sensor 110S. FIG. 15B is a diagram illustrating an exemplary connection configuration of the sensor 110R. FIG. 15C is a diagram illustrating an exemplary connection configuration of the heater 19. The heater 19 according to the present embodiment is similarly configured to the heater 19 illustrated in FIG. 4C, and thus the detailed description thereof will be omitted herein.

A gas sensor 101 according to the present embodiment includes a sensor unit 110, the current measurement unit 20, the gas density measurement unit 30, the power supply unit 40, the control unit 50, and the data I/O unit 90 as illustrated in FIG. 1.

The sensor unit 110 includes the sensor (first capacitor-type sensor) 110S, the sensor (second capacitor-type sensor) 110R, and the heater 19 as illustrated in FIG. 1. The sensor 110S includes a semiconductor substrate (third semiconductor substrate) 111S, a well (third well) 112S, a gate insulative film (third gate insulative film) 115S, a gate layer (third gate layer) 116S, and a gate protective film 117S as illustrated in FIG. 14A. The sensor 110S is configured such that the well 112S, the gate insulative film 115S, the gate layer 116S, and the gate protective film 117S are sequentially laminated on the semiconductor substrate 111S as illustrated in FIG. 14A.

The semiconductor substrate 111S, the well 112S, the gate insulative film 115S, the gate layer 116S, and the gate protective film 117S are similar in their configurations to the semiconductor substrate 11S, the well 12S, the gate insulative film 15S, the gate layer 16S, and the gate protective film 17S illustrated in FIG. 2A, respectively. That is, part of a surface of the gate layer 116S is exposed to the atmosphere also in the sensor 110S.

The sensor 110R includes a semiconductor substrate (fourth semiconductor substrate) 111R, a well (fourth well) 112R, a gate insulative film (fourth gate insulative film) 115R, a gate layer (fourth gate layer) 116R, and a gate protective film (second gate protective film) 117R as illustrated in FIG. 14B. The sensor 110R is configured such that the well 112R, the gate insulative film 115R, the gate layer 116R, and the gate protective film 117R are sequentially laminated on the semiconductor substrate 111R as illustrated in FIG. 14B.

The semiconductor substrate 111R, the well 112R, the gate insulative film 115R, the gate layer 116R, and the gate protective film 117R are similar in their configurations to the semiconductor substrate 11R, the well 12R, the gate insulative film 15R, the gate layer 16R, and the gate protective film 17R illustrated in FIG. 2B, respectively. That is, a surface of the gate layer 116R is covered with the gate protective film 117R and is not exposed to the atmosphere also in the sensor 110R.

The well 112S and the gate layer 116S in the sensor 110S are connected to the power supply unit 40, the current measurement unit 20, and the like illustrated in FIG. 1 via a wiring layer (not illustrated). The well 112R and the gate layer 116R in the sensor 110R are also connected to the power supply unit 40, the current measurement unit 20, and the like via a wiring layer (not illustrated).

The description will be made below assuming that the wells 112S and 112R are of N-type. The wells 112S and 112R may be of P-type, or one well may of N-type and the other well may be of P-type.

For example, the wells 112S and 112R in the sensors 110S and 110R are connected to the power supply 41 for applying a periodically-changing AC voltage such as sine wave as illustrated in FIGS. 15A and 15B. The gate layers 116S and 116R in the sensors 110S and 110R are connected to the power supply for applying a variable voltage as illustrated in FIGS. 15A and 15B. The gate layers 116S and 116R are connected to the current measurement unit 20 as illustrated in FIGS. 15A and 15B.

A capacitance (first capacitance) of the sensor 110S is measured on the basis of the voltage applied to the gate layer 116S, the voltage (such as AC voltage) applied to the well 112S, and the current (first gate current such as AC current) flowing in the gate layer 116S. A capacitance (second capacitance) of the sensor 110R is measured on the basis of the voltage applied to the gate layer 116R, the AC voltage applied to the well 112R, the current (second gate current such as AC current) flowing in the gate layer 116R. The capacitances are measured by the gas density measurement unit 30 or the like, for example.

The current measurement unit 20 measures the current flowing in the gate layer 116S in the sensor 110S, for example. The current measurement unit 20 measures the current flowing in the gate layer 116R in the sensor 110R, for example.

The gas density measurement unit 30 measures the capacitance (first capacitance) of the sensor 110S on the basis of the voltage applied to the gate layer 116S, the voltage (such as AC voltage) applied to the well 112S, and the current such as AC current flowing in the gate layer 116S, for example.

The gas density measurement unit 30 measures the capacitance (second capacitance) of the sensor 110R on the basis of the voltage applied to the gate layer 116R, the voltage such as AC voltage applied to the well 112R, and the current such as AC current flowing in the gate layer 116R, for example.

Figure 16A:
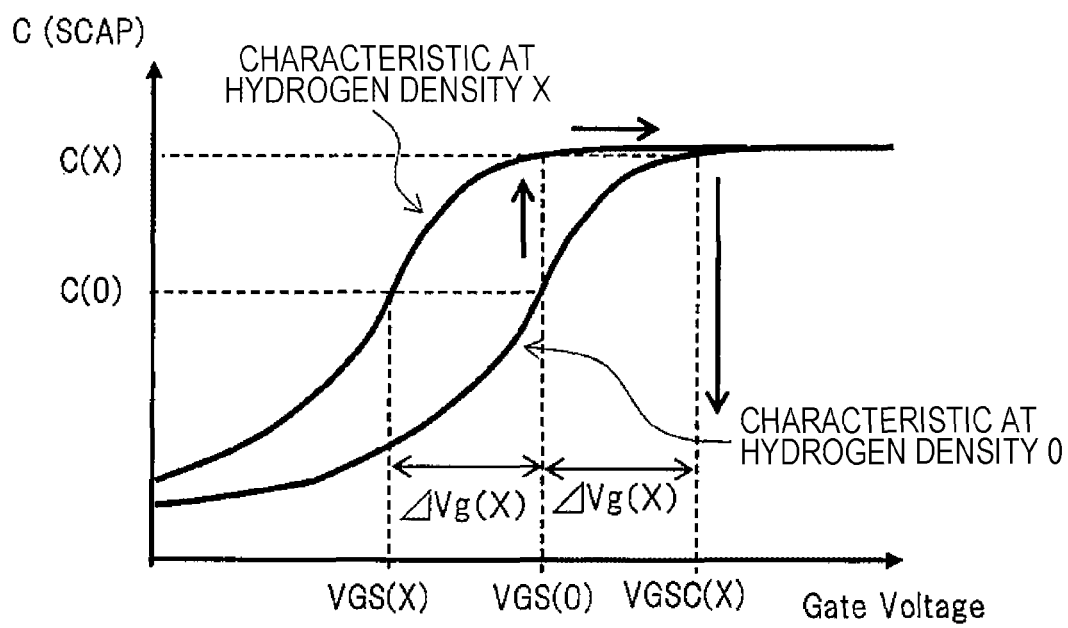
FIGS. 16A and 16B are diagrams illustrating exemplary voltage-capacitance characteristics of sensors according to the fourth embodiment of the present invention.
Figure 16B:
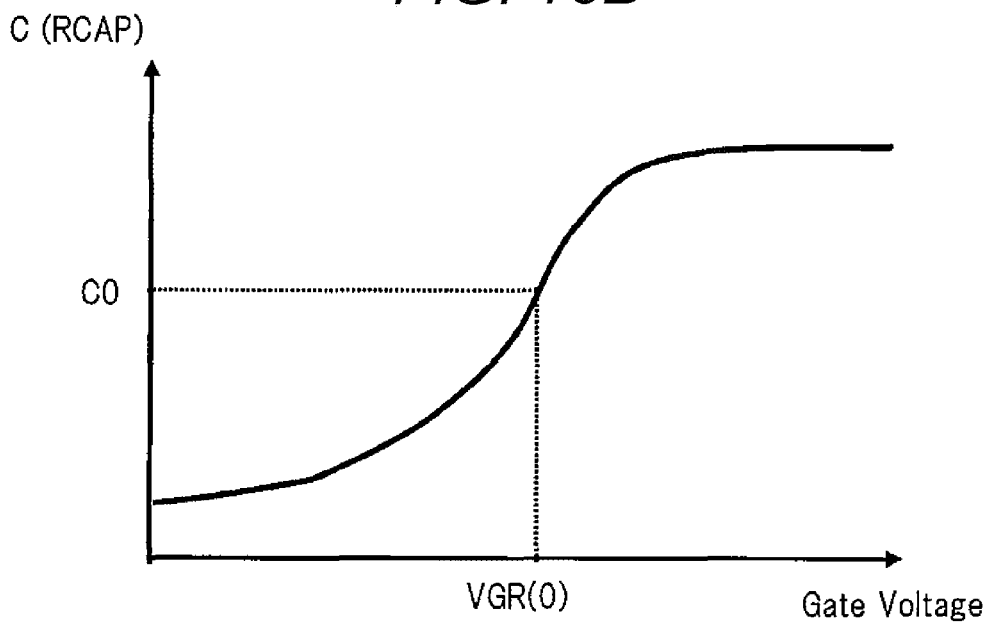

FIGS. 16A and 16B are diagrams illustrating exemplary voltage-capacitance characteristics of the sensors according to the fourth embodiment of the present invention. FIG. 16A is a diagram illustrating a gate voltage-capacitance characteristic of the sensor 110S. FIG. 16B is a diagram illustrating a gate voltage-capacitance characteristic of the sensor 110R. A surface of the gate layer 116S is exposed in the sensor 110S, and thus as the gas density is higher, the gate voltage-capacitance characteristic of the sensor 110S moves leftward in parallel as illustrated in FIG. 16A. That is, the voltage of the gate layer 116S changes from a threshold voltage (fifth threshold voltage) VGS(0) to a threshold voltage (sixth threshold voltage) VGS(X) when the capacitance of the sensor 110S is a threshold capacitance C(0), and is lower as the gas density is higher.

<Gas Density Measurement Method>

A gas density measurement method according to the present embodiment will be described below. The description will be made below assuming that the gas density of hydrogen gas as exemplary gas to be detected is measured.

At first, the control unit 50 adjusts the temperature of the sensor unit 110. The control unit 50 then applies a voltage to each unit in the sensors 110S and 110R. For example, a power supply 41 applies a predetermined AC voltage to the well 112S. A power supply 41 applies the predetermined threshold voltage VGS(0) to the gate layer 116S such that the capacitance of the sensor 110S is the threshold capacitance C(0). A power supply 41 applies a predetermined AC voltage to the well 112R. A power supply 41 applies a predetermined threshold voltage (seventh threshold voltage) VGR(0) to the gate layer 116R such that the capacitance of the sensor 110R is the threshold capacitance C(0).

The threshold voltages VGS(0) and VGR(0) of the sensors 110S and 110R at a gas density of 0 may be previously measured. The control unit 50 may read the data on the previously-measured threshold voltages VGS(0) and VGR(0) from the data storage unit (not illustrated) as needed, for example. The control unit 50 outputs the data on the threshold voltages VGS(0) and VGR(0) to the gas density measurement unit 30, for example.

The control unit 50 then measures the threshold voltages VGS(X) and VGR(X) of the sensors 110S and 110R in the hydrogen gas atmosphere. The gate layer 116R in the sensor 110R is isolated from the atmosphere by the gate protective film 117R, and thus a threshold voltage (eighth threshold voltage) VGR(X) of the sensor 110R matches with the threshold voltage VGR(0) at a gas density of 0. The control unit 50 outputs the data on the threshold voltages VGS(X) and VGR(X) of the sensors 110S and 110R to the gas density measurement unit 30, for example.

The gas density measurement unit 30 then measures the gas density of the hydrogen gas. For example, the gas density measurement unit 30 measures the gas density of the hydrogen gas at a predetermined time on the basis of a threshold change (fourth threshold change) $\Delta Vg(X)$ as a difference between an inter-sensor potential difference (third inter-sensor potential difference) as a difference between the threshold voltage VGR(0) applied to the gate layer 116R when the capacitance of the sensor 110R is the threshold capacitance C(0) and the threshold voltage VGS(0) applied to the gate layer 116S when the capacitance of the sensor 110S is the threshold capacitance C(0) while the hydrogen gas is not present in the atmosphere, and an inter-sensor potential difference (fourth inter-sensor potential difference) as a difference between the threshold voltage VGR(X) applied to the gate layer 116R when the capacitance of the sensor 110R is the threshold capacitance C(0) at the predetermined time and the threshold voltage VGS(X) applied to the gate layer 116S when the capacitance of the sensor 110S is the threshold capacitance C(0) at the predetermined time while the hydrogen gas is present in the atmosphere, and a temporal differentiation $d\Delta Vg(X)/dt$ of the threshold change.

Specifically, the gas density measurement unit 30 measures the gas density X in the atmosphere on the basis of the threshold voltages VGS(0), VGR(0), VGS(X), and VGR(X) output from the control unit 50, and (Equation 1) to (Equation 8).

Also according to the present embodiment, if a variation in the threshold voltages of the sensor 110S due to noise is small, the gas density measurement unit 30 may measure the gas density by only the sensor 110S. For example, the gas density measurement unit 30 measures the gas density of the hydrogen gas at a predetermined time on the basis of a threshold change (third threshold change) $\Delta Vg(X)$ as a difference between the threshold voltage VGS(0) and the threshold voltage VGS(X) of the sensor 110S, and a temporal differentiation $d\Delta Vg(X)/dt$ of the threshold change.

[Other Gas Density Measurement Method]

The gas density in the atmosphere may be measured by use of a similar method to the second embodiment according to the present embodiment. The power supply 41 keeps applying the threshold voltage VGS(0) to the gate layer 116S also after the gas density starts being measured as illustrated in FIG. 16A, for example.

In the meanwhile, the gas density measurement unit 30 measures a capacitance C(X) of the sensor 110S in the hydrogen gas atmosphere, for example. The gas density measurement unit 30 then detects the voltage VGSC(X) of the gate layer 116S with the capacitance C(X) at a gas density of 0 with reference to the database corresponding to the gate voltage-capacitance characteristic illustrated in FIG. 16A.

The gas density measurement unit 30 then calculates the threshold change $\Delta Vg(X)$ at a gas density of X on the basis of the voltage VGSC(X) and the threshold voltage VGS(0) of the sensor 110S, and (Equation 10). The gas density measurement unit 30 then calculates the gas density X on the basis of (Equation 8) and (Equation 10), It is preferable to create a database in which the voltage VGSC(X) at a gas density of X detected while the gate voltage is kept constant is associated with the threshold voltage VGS(X) at a gas density of X detected while the capacitance is kept constant when the waveform of the gate voltage-capacitance characteristic of the sensor 110S varies depending on the gas density. Thereby, the gas density measurement unit 30 can detect the threshold voltage VGS (X) on the basis of the measured voltage VGSC(X) with reference to the database, and can accurately measure the gas density.

The following effects according to the present embodiment can be obtained in addition to the effects according to the above embodiments. According to the present embodiment, the gas density measurement unit 30 measures the gas density of the gas to be detected on the basis of the threshold change $\Delta Vg(X)$ calculated from the threshold voltages VGS (0), VGS(X), VGR(0), and VGR(X) of the sensors 110S and 110R, and the temporal differentiation $d\Delta Vg(X)/dt$ of the threshold change. With the configuration, the gas density is measured also while a chemical reaction with the gas to be detected in the sensor 110S is in the non-equilibrium state, and thus the gas density can be measured in a short time also when capacitors are used for the sensors 110S and 110R.

A periodically-changing AC voltage is applied to the well 112S and the well 112R according to the present embodiment. With the configuration, an AC current flows in the gate layers 116S and 116R, and thus the capacitances of the sensors 110S and 110R can be easily measured.

According to the present embodiment, the gas density measurement unit 30 calculates the threshold change $\Delta Vg$ (X) by measuring the capacitance C(X) when the voltage applied to the gate layer 116S in the sensor 110S is kept at the threshold voltage VGS(0). With the configuration, the voltage applied to the gate layer 116S is kept constant while the gas density is being measure, thereby alleviating loads on the gas density measurement.

Fifth Embodiment

A fifth embodiment of the present invention will be described below. The description of the parts common with the above embodiments will be basically omitted below. A gas sensor using a diode for a sensor unit will be described according to the present embodiment.

Figure 17A:
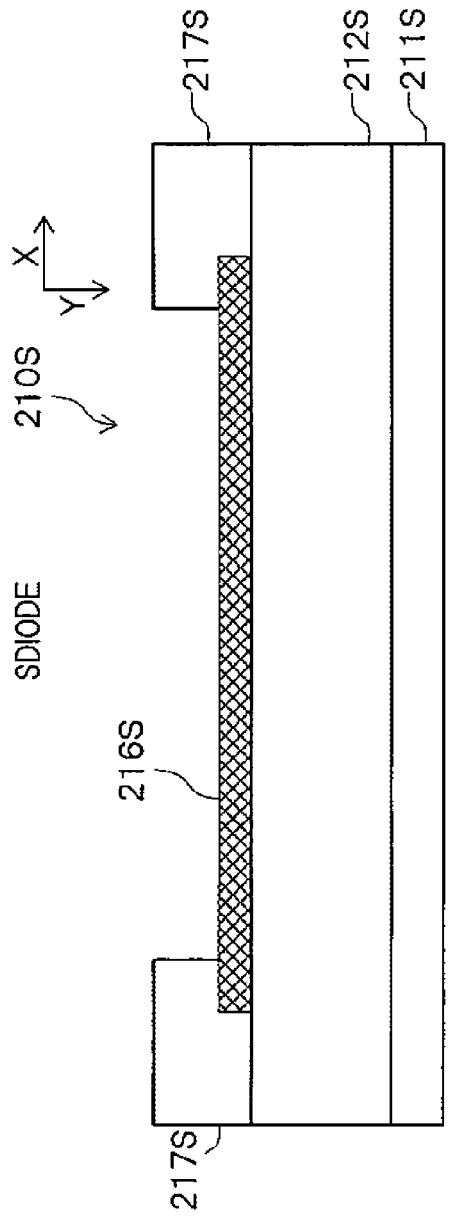
FIGS. 17A and 17B are cross-section views illustrating exemplary configurations in a sensor unit according to a fifth embodiment of the present invention.
Figure 17B:
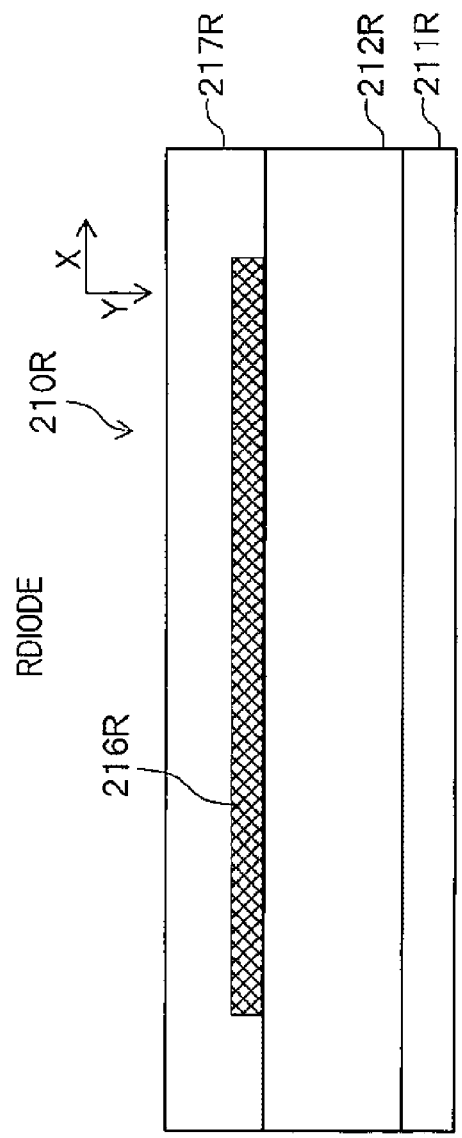
Figure 18A:
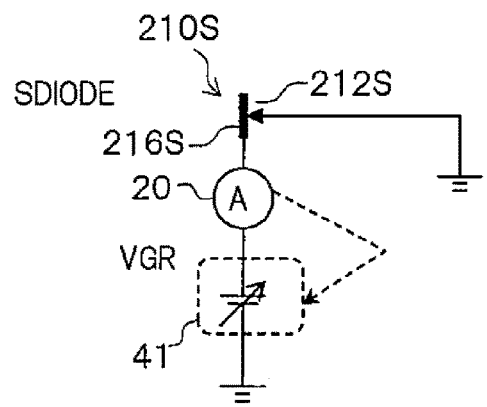
FIGS. 18A to 18C are diagrams illustrating exemplary connection configurations in the sensor unit according to the fifth embodiment of the present invention.
Figure 18B:
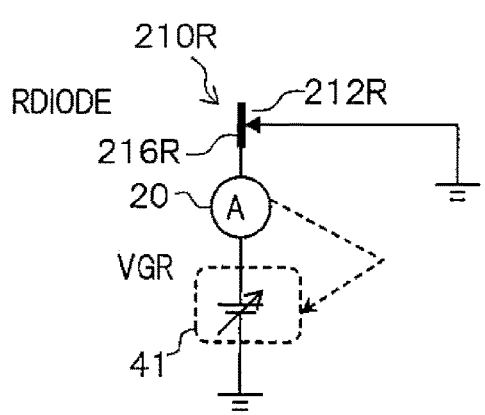
Figure 18C:
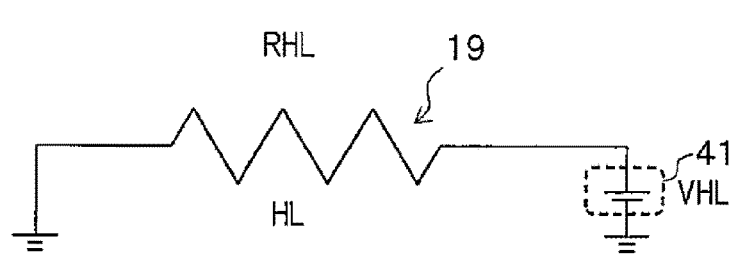

FIGS. 17A and 17B are cross-section views illustrating exemplary configurations in a sensor unit according to the fifth embodiment of the present invention. FIG. 17A is a cross-section view of a sensor 210S, and FIG. 17B is a cross-section view of a sensor 210R. FIGS. 18A to 18C are diagrams illustrating exemplary connection configurations in the sensor unit according to the fifth embodiment of the present invention. FIG. 18A is a diagram illustrating an exemplary connection configuration of the sensor 210S. FIG. 18B is a diagram illustrating an exemplary connection configuration of the sensor 210R. FIG. 18C is a diagram illustrating an exemplary connection configuration of the heater 19. The heater 19 according to the present embodiment is similarly configured to the heater 19 illustrated in FIG. 4C, for example, and thus the detailed description thereof will be omitted herein.

A gas sensor 201 according to the present embodiment includes a sensor unit 210, the current measurement unit 20, the gas density measurement unit 30, the power supply unit 40, the control unit 50, and the data I/O unit 90 as illustrated in FIG. 1.

The sensor unit 210 includes the sensor (first diode-type sensor) 210S, the sensor (second diode-type sensor) 210R, and the heater 19 as illustrated in FIG. 1. The sensor 210S includes a semiconductor substrate (fifth semiconductor substrate) 211S, a well (fifth well) 212S, a gate layer (fifth gate layer) 216S, and a gate protective film 217S as illustrated in FIG. 17A. The sensor 210S is configured such that the well 212S, the gate layer 216S, and the gate protective film 217S are sequentially laminated on the semiconductor substrate 211S as illustrated in FIG. 17A.

The semiconductor substrate 211S, the well 212S, the gate layer 216S, and the gate protective film 217S are similar in their configurations to the semiconductor substrate 11S, the well 12S, the gate layer 16S, and the gate protective film 17S illustrated in FIG. 2A, respectively. That is, part of a surface of the gate layer 216S is exposed to the atmosphere also in the sensor 210S.

The sensor 210R includes a semiconductor substrate (sixth semiconductor substrate) 211R, a well (sixth well) 212R, a gate layer (sixth gate layer) 216R, and a gate protective film (second gate protective film) 217R as illustrated in FIG. 17B. The sensor 210R is configured such that the well 212R, the gate layer 216R, and the gate protective film 217R are sequentially laminated on the semiconductor substrate 211R as illustrated in FIG. 17B.

The semiconductor substrate 211R, the well 212R, the gate layer 216R, and the gate protective film 217R are similar in their configurations to the semiconductor substrate 11R, the well 12R, the gate layer 16R, and the gate protective film 17R illustrated in FIG. 2B, respectively. That is, a surface of the gate layer 216R is covered with the gate protective film 217R and is not exposed to the atmosphere also in the sensor 210R.

The description will be made below assuming that the wells 212S and 212R are of N-type. The wells 212S and 212R may be of P-type, or one well may be of N-type and the other well may be of P-type.

The well 212S and the gate layer 216S in the sensor 210S are connected to the power supply unit 40, the current measurement unit 20, and the like illustrated in FIG. 1 via a wiring layer (not illustrated). The well 212R and the gate layer 216R in the sensor 210R are also connected to the power supply unit 40, the current measurement unit 20, and the like via a wiring layer (not illustrated).

For example, the wells 212S and 212R in the sensors 210S and 210R are connected to the power supply 41 for applying a predetermined voltage as illustrated in FIGS. 18A and 18B. The wells 212S and 212R may be grounded as illustrated in FIGS. 18A and 18B. The gate layers 216S and 216R in the sensors 210S and 210R are connected to the power supply 41 for applying a variable voltage as illustrated in FIGS. 18A and 18B. The gate layers 216S and 216R are connected to the current measurement unit 20 as illustrated in FIGS. 18A and 18B.

The current measurement unit 20 measures a diode current (first diode current) flowing between the gate layer 216S and the well 212S in the sensor 210S, for example. The current measurement unit 20 measures a diode current (second diode current) flowing between the gate layer 216R and the well 212R in the sensor 210R, for example.

Figure 19A:
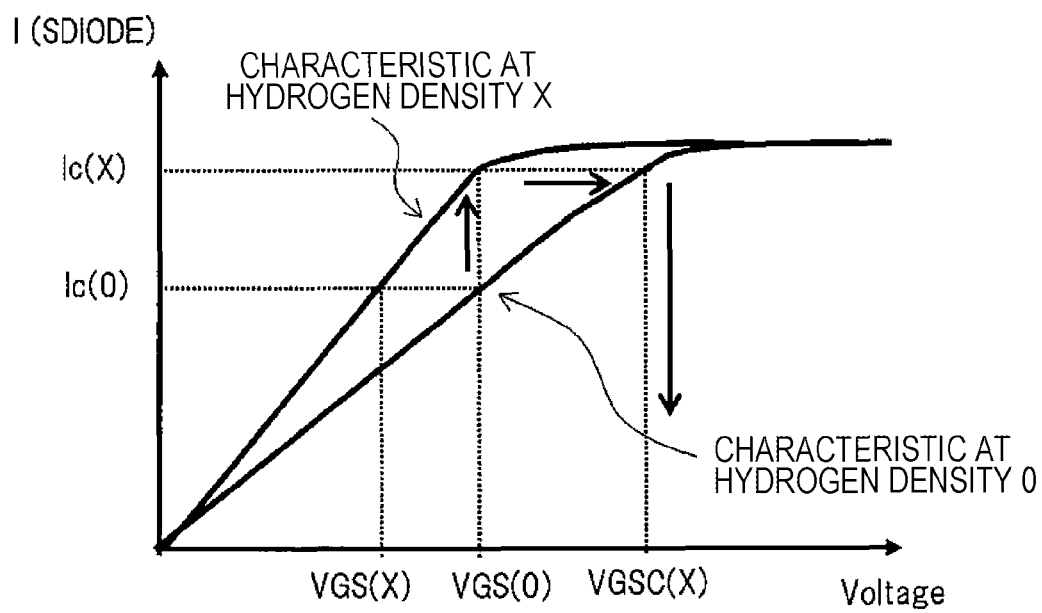
FIGS. 19A and 19B are diagrams illustrating exemplary gate voltage-current characteristics of sensors according to the fifth embodiment of the present invention.
Figure 19B:
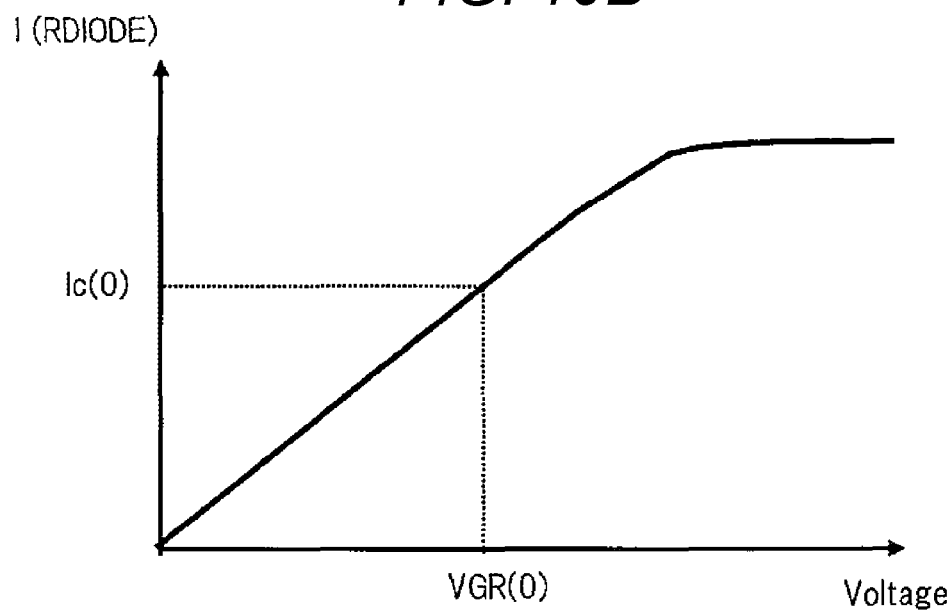

FIGS. 19A and 19B are diagrams illustrating exemplary gate voltage-current characteristics of the sensors according to the fifth embodiment of the present invention. FIG. 19A is a diagram illustrating a gate voltage-current characteristic of the sensor 210S. FIG. 19B is a diagram illustrating a gate voltage-current characteristic of the sensor 210R. FIGS. 19A and 19B illustrate the gate voltage-current characteristics when a forward bias is applied to the sensors 210S and 210R.

A surface of the gate layer 216S is exposed in the sensor 210S, and thus as the gas density is higher, the gate voltage-current characteristic of the sensor 210S moves leftward in parallel and its waveform changes as illustrate in FIG. 19A. That is, the voltage of the gate layer 216S changes from a threshold voltage (ninth threshold voltage) VGS(0) at a gas density of 0 to a threshold voltage (tenth threshold voltage) VGS(X) at a gas density of X when the diode current of the sensor 210S is a threshold current (second threshold current) Ic(0), and is lowers as the gas density is higher.

<Gas Density Measurement Method>

A gas density measurement method according to the present embodiment will be described below. The description will be made below assuming that the gas density of hydrogen gas as exemplary gas to be detected is measured.

At first, the control unit 50 adjusts the temperature of the sensor unit 210. The control unit 50 then applies a voltage to each unit in the sensors 210S and 210R. For example, a power supply 41 applies a predetermined voltage to the well 212S. A power supply 41 applies the predetermined threshold voltage VGS(0) to the gate layer 216S such that the diode current of the sensor 210S is the threshold current Ic(0). A power supply 41 applies a predetermined voltage to the well 212R. A power supply applies a predetermined threshold voltage (11th threshold voltage) VGR(0) to the gate layer 216R such that the diode current of the sensor 210R is the threshold current (second threshold current) Ic(0).

The threshold voltages VGS(0) and VGR(0) of the sensors 210S and 210R at a gas density of 0 may be previously measured. The control unit 50 may read the data on the previously-measured threshold voltages VGS(0) and VGR(0) from the data storage unit (not illustrated) as needed, for example. The control unit 50 outputs the data on the threshold voltages VGS(0) and VGR(0) to the gas density measurement unit 30, for example.

The control unit 50 then measures the threshold voltages VGS(X) and VGR(X) of the sensors 210S and 210R in the hydrogen gas atmosphere. The gate layer 216R in the sensor 210R is isolated from the atmosphere by the gate protective film 217R, and thus a threshold voltage (12th threshold voltage) VGR(X) of the sensor 210R matches with the threshold voltage VGR(0) at a gas density of 0. The control unit 50 outputs the data on the threshold voltages VGS(X) and VGR(X) of the sensors 210S and 210R to the gas density measurement unit 30, for example.

The gas density measurement unit 30 then measures the gas density of the hydrogen gas. For example, the gas density measurement unit 30 measures the gas density of the hydrogen gas at a predetermined time on the basis of a threshold change (sixth threshold change) $\Delta Vg(X)$ as a difference between an inter-sensor potential difference (fifth inter-sensor potential difference) between the threshold voltage VGR(0) applied to the gate layer 216R when the diode current of the sensor 210R is the threshold current Ic(0) and the threshold voltage VGS(0) applied to the gate layer 216S when the diode current of the sensor 210S is the threshold current Ic(0) while the hydrogen gas is not present in the atmosphere, and an inter-sensor potential difference (sixth inter-sensor potential difference) as a difference between the threshold voltage VGR(X) applied to the gate layer 216R when the diode current of the sensor 210R is the threshold current Ic(0) at the predetermined time and the threshold voltage VGS(X) applied to the gate layer 216S when the diode current of the sensor 210S is the threshold current Ic(0) while the hydrogen gas is present in the atmosphere, and a temporal differentiation $d\Delta Vg(X)/dt$ of the threshold change.

Specifically, the gas density measurement unit 30 measures the gas density X in the atmosphere on the basis of the threshold voltages VGS(0), VGR(0), VGS(X) and VGR(X) output from the control unit 50, and (Equation 1) to (Equation 8).

Also according to the present embodiment, if a variation in the threshold voltages of the sensor 210S due to noise is small, the gas density measurement unit 30 may measure the gas density by only the sensor 210S. For example, the gas density measurement unit 30 measures the gas density of the hydrogen gas at a predetermined time on the basis of a threshold change (fifth threshold change) $\Delta Vg(X)$ as a difference between the threshold voltage VGS(0) and the threshold voltage VGS(X) of the sensor 210S, and a temporal differentiation $d\Delta Vg(X)/dt$ of the threshold change.

The threshold current Ic (0) takes an appropriate value, thereby restricting an effect of noise due to a change in temperature. Also in this case, the gas density measurement unit 30 can measure the gas density by only the sensor 210S.

A reverse bias may be applied to the sensors 210S and 210R. When a reverse bias is applied, little current flows between the gate layer 216S and the well 212S. In this case, however, the gas density can be measured by use of a phenomenon that the depletion layer capacitances of the diodes change due to the hydrogen density.

For example, the gate voltage-capacitance characteristics of the sensors 210S and 210R per gas density when a reverse bias is applied are compiled into a database. Similarly to the capacitor-using gas sensor, the gas density measurement unit 30 measures the threshold change $\Delta Vg(X)$ on the basis of the changes in the gate voltage-capacitance characteristics of the sensors 210S and 210R.

[Other Gas Density Measurement Method]

The gas density in the atmosphere may be measured in a similar method to the second embodiment according to the present embodiment. The power supply 41 keeps applying the threshold voltage VGS(0) to the gate layer 216S also after the gas density starts being measured as illustrated in FIG. 19, for example.

In the meanwhile, the gas density measurement unit 30 acquires the information on the diode current of the sensor 210S in the hydrogen gas atmosphere, for example. The gas density measurement unit 30 then detects the voltage VGSC (X) of the gate layer 216S with the diode current Ic(X) at a gas density of 0 with reference to the database corresponding to the gate voltage-current characteristic illustrated in FIG. 19.

The gas density measurement unit 30 then calculates the threshold change $\Delta Vg(X)$ at a gas density of X on the basis of the voltage VGSC(X) and the threshold voltage VGS(0) of the sensor 210S, and (Equation 10). The gas density measurement unit 30 then calculates the gas density X on the basis of (Equation 8) and (Equation 10).

It is preferable to create a database in which the voltage VGSC(X) at a gas density of X detected while the gate voltage is kept constant is associated with the threshold voltage VGS(X) at a gas density of X detected while the diode current is kept at the threshold current Ic(0) when the waveform of the gate voltage-capacitance characteristic of the sensor 210S changes due to the gas density. Thereby, the gas density measurement unit 30 can detect the threshold voltage VGS(X) on the basis of the measured voltage VGSC(X) with reference to the database, and can accurately measure the gas density.

The following effects according to the present embodiment can be obtained in addition to the effects according to the above embodiments. According to the present embodiment, the gas density measurement unit 30 measures the gas density of the gas to be detected on the basis of the threshold change $\Delta Vg(X)$ calculated from the threshold voltages VGS (0), VGS(X), VGR(0), and VGR(X) of the sensors 210S and 210R, and the temporal differentiation $d\Delta Vg(X)/dt$ of the threshold change. With the configuration, the gas density is measured also when a chemical reaction with the gas to be detected in the sensor 210S is in the non-equilibrium state, and thus the gas density can be measured in a short time also when diodes are used for the sensors 210S and 210R.

According to the present embodiment, the gas density measurement unit 30 calculates the threshold change $\Delta Vg$ (X) by measuring the diode current Ic(X) when the voltage applied to the gate layer 216S in the sensor 210S is kept at the threshold voltage VGS(0). With the configuration, the voltage applied to the gate layer 216S is kept constant while the gas density is being measured, thereby alleviating loads on the gas density measurement.

Sixth Embodiment

A sixth embodiment of the present invention will be described below. The above embodiments assume that a gas density of hydrogen gas is measured. A gas sensor for measuring a gas density of other than hydrogen gas will be described according to the present embodiment.

Figure 20:
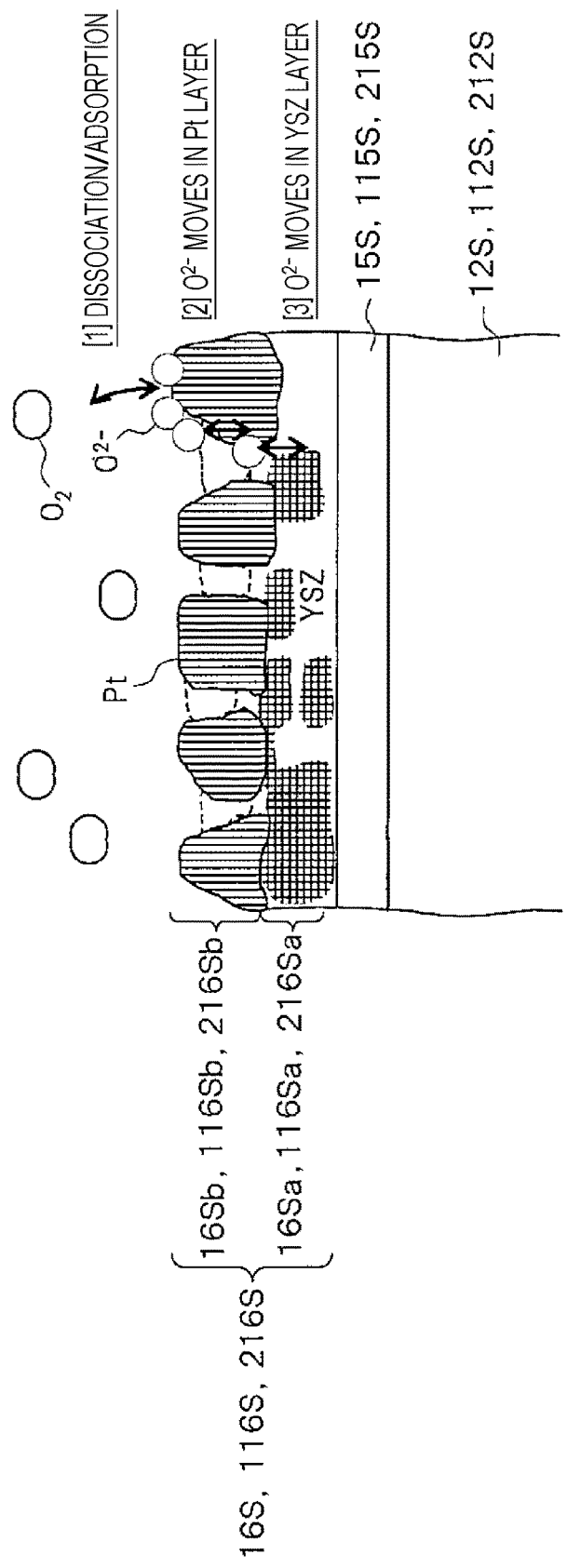
FIG. 20 is a diagram illustrating how the gate layer reacts with oxygen gas according to a sixth embodiment of the present invention.

A gas sensor for measuring a gas density of oxygen gas will be described herein. FIG. 20 is a diagram illustrating how a gate layer reacts with oxygen gas according to the sixth embodiment of the present invention. According to the present embodiment, the electrode support layer 16Sa (116Sa, 216Sa) of the gate layer 16S (116S, 216S) in the sensor 10S (110S, 210S) is made of yttria-doped zirconia or yttria-stabilized zirconia (YSZ) as illustrated in FIG. 20, for example.

Oxygen molecules are dissociated/adsorbed on the electrode layer 16Sb (116Sb, 216Sb) of the gate layer 16S (116S, 216S) as illustrated in FIG. 20. Part of oxygen atoms ($O^{2-}$) dissociated in the electrode layer 16Sb (116Sb, 216Sb) moves from the electrode layer 16Sb (116Sb, 216Sb) to the electrode support layer 16Sa (116Sa, 216Sa). Part of oxygen atoms ($O^{2-}$) in the electrode support layer 16Sa (116Sa, 216Sa) moves to the electrode layer 16Sb (116Sb, 216Sb). The dissociation/adsorption of the oxygen atoms in the electrode layer 16Sb (116Sb, 216Sb) enters the equilibrium state after a certain period of time. The oxygen ions generated by the dissociated oxygen molecules are negatively charged. The sign of the charges of the oxygen ions is reverse to that of the hydrogen ions. Thus, the threshold change $\Delta Vg(X)$ of the oxygen gas shifts to positive as the gas density is higher. That is, the sign of the threshold change $\Delta Vg(X)$ in the oxygen gas in (Equation 2) is reverse to that of the hydrogen gas. However, the absolute value of the threshold change $\Delta Vg(X)$ is used for the oxygen gas, and thus the gas density of the oxygen gas is measured on the basis of the dissociation/adsorption system.

A gas sensor for measuring a gas density of gas to be detected other than the gas will be described below. (Equation 3) to (Equation 5) are for explaining the Langmuir dissociation/adsorption phenomenon, and the equations are established when gas to be detected is made of diatomic molecules containing atoms of the same kind such as hydrogen gas and oxygen gas.

Generally, the adsorption speed V1 and the desorption speed V2 are expressed by the occupancy θ of the adsorption site and the gas density X of the gas to be detected in the atmosphere as follows.

$$V1 = k1 \times (1-\theta)^n \times X \qquad \text{(Equation 11)}$$

$$V2 = k2 \times \theta^n \qquad \text{(Equation 12)}$$

A temporal differentiation $d\theta/dt$ of the occupancy θ is expressed by use of (Equation 11) and (Equation 12) as follows.

$$d\theta/dt = V1 - V2 = k1 \times (1-\theta)^n \times X - k2\theta^n \qquad \text{(Equation 13)}$$

The gas density X is expressed in the following Langmuir equation according to (Equation 13).

$$X = [\Delta Vgmax \times (d\Delta Vg(X)/dt) + k2 \times (\Delta Vg(X))^n]/[k1 \times (\Delta Vgmax - \Delta Vg(X))^n] \qquad \text{(Equation 14)}$$

where $\Delta Vgmax$, k1, and k2 are parameters depending on the temperature at the time of measurement of the gas density, the material and quality of the gate layer 16S (116S, 216S), and the like. The index n indicates the number of hydrogen atoms or oxygen atoms contained in the gas molecules of the gas to be detected.

For example, when the gas to be detected is made of diatomic molecules containing atoms of the same kind, the index n is 2. In this case, (Equation 11) to (Equation 14) are the same as (Equation 3) to (Equation 5) and (Equation 8). When the gas to be detected is made of monoatomic molecules, the index n is 1.

When the electrode support layer 16Sa (116Sa, 216Sa) is made of a material capable of adsorbing oxygen ions such as YSZ, the threshold voltage changes for the gas containing oxygen atoms such as sulfur oxide ($SO_x$) or nitrogen oxide ($NO_x$) in the sensor 10S (110S, 210S). For example, the indexes n of the gas to be detected SO, $SO_2$, $SO_3$, NO, and $NO_2$ are set at 1, 2, 3, 1, and 2, respectively, and the gas densities of them are measured.

On the other hand, when the electrode support layer 16Sa (116Sa, 216Sa) is made of a material capable of adsorbing hydrogen ions such as titanium oxide, the threshold voltage changes for the gas containing hydrogen atoms in the sensor 10S (110S, 210S). For example, the indexes n of hydrogen fluoride (HF), hydrogen chloride (HCl), hydrogen sulfide (H₂S) and ammonium (NH₃) are set at 1, 1, 2, and 3, respectively, and the gas densities of them are measured.

Nitrogen monoxide (NO), hydrogen sulfide (H₂S), and ammonium (NH₃) are contained in the breath of a person, and may be used as a marker for detecting a disease.

The following effects according to the present embodiment can be obtained in addition to the effects according to the above embodiments. According to the present embodiment, the parameters and index are set depending on the gas to be detected, and thus the gas densities of some types of gas to be detected can be measured by only one gas sensor.

According to the present embodiment, the gate layer 16S (116S, 216S) is configured such that the electrode support layer 16Sa (116Sa, 216Sa) made of yttria-stabilized zirconia and the electrode layer 16Sb (116Sb, 216Sb) made of platinum are laminated, and the gas density measurement unit 30 sets the index in the Langmuir equation depending on the number of oxygen atoms in the molecules of the gas to be detected. With the configuration, the parameters and index depending on the kind of the gas to be detected are used, thereby accurately measuring the gas density of the gas containing oxygen atoms.

According to the present embodiment, the gas density measurement unit 30 sets the index in the Langmuir equation at 2, and measures the gas density of the oxygen gas. With the configuration, the Langmuir equation for the oxygen gas is used and thus the gas density of the oxygen gas is accurately measured.

Seventh Embodiment

A seventh embodiment of the present invention will be described below. The method for measuring a gas density by use of the preset parameters k1, k2, and ΔVgmax has been described according to the above embodiments. In many cases, however, aged deterioration of the response performance of the sensor 10S (110S, 210S) is caused over time in the gas sensor 1 (101, 201). Combustible adhered materials are deposited on the surface of the adsorption site of the gate layer 16S (116S, 216S), for example, and thus the aged deterioration is caused. In this case, for example, the control unit 50 causes the heater 19 to be applied with a higher voltage than normal, and sets the sensor unit 10 (110, 210) at a high temperature. Thereby, the adhered materials on the gate layer 16S (116S, 216S) are burned and are removed from the adsorption site. In this way, the heater 19 performs a refresh operation of burning the adhered materials in the sensor 10S (110S, 210S).

To the contrary, when adhered materials are not combustible or when combustion-supporting gas is not present in the atmosphere and adhered materials cannot be burned, the parameters need to be changed in consideration of the aged deterioration. Thus, a gas sensor for aged deterioration of the response characteristic will be described according to the present embodiment. The description of the parts common with the above embodiments will be basically omitted below.

Figure 21:
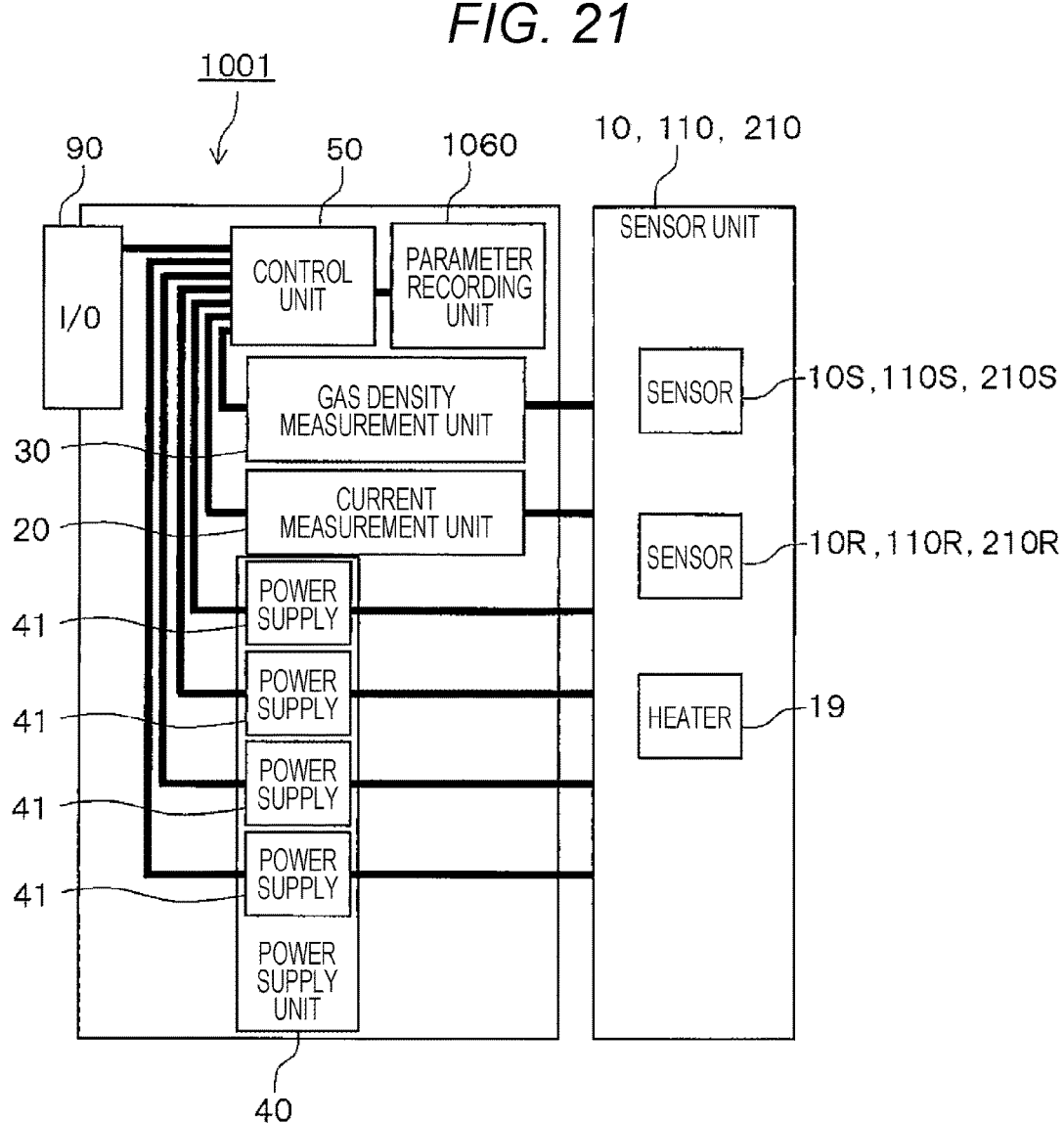
FIG. 21 is a diagram illustrating an exemplary configuration of a gas sensor according to seventh and eighth embodiments of the present invention.

FIG. 21 is a diagram illustrating an exemplary configuration of a gas sensor according to seventh and eighth embodiments of the present invention. A gas sensor 1001 according to the present embodiments includes the sensor unit 10 (110, 210), the current measurement unit 20, the gas density measurement unit 30, the power supply unit 40, the control unit 50, the data I/O unit 90, and a parameter recording unit 1060 as illustrated in FIG. 21.

The parameter recording unit 1060 is configured of a recording medium such as nonvolatile memory. The parameter recording unit 1060 records therein aged deterioration information of the sensor unit 10 (110, 210). For example, the parameter recording unit 1060 records therein an operating time and the like of the sensor unit 10 (110, 210) as the aged deterioration information. The parameter recording unit 1060 records therein the parameters for the aged deterioration information such as the operating time of the sensor unit 10 (110, 210). For example, the parameter recording unit 1060 records therein a table, database, or the like in which the aged deterioration information is associated with the parameters k1, k2, and ΔVgmax corresponding to the aged deterioration information on the basis of a previously-made deterioration test.

The control unit 50 or the gas density measurement unit 30 may measure the operating time as an operating time measurement unit for measuring the operating time of the sensor unit 10 (110, 210). The gas sensor 1001 may additionally include an operating time measurement unit for measuring the operating time of the sensor unit 10 (110, 210). The operating time measurement unit is configured of a counter or timer having a counting function, for example.

The gas density measurement unit 30 measures the gas density of the gas to be detected on the basis of the operating time of the sensor unit 10 (110, 210) and the parameters corresponding to the operating time of the sensor unit 10 (110, 210). For example, the control unit 50 reads the parameters corresponding to the measured operating time from the parameter recording unit 1060. The control unit 50 then outputs the read parameters to the gas density measurement unit 30, for example. The gas density measurement unit 30 measures the gas density on the basis of the parameters output from the control unit 50.

The following effects according to the present embodiment can be obtained in addition to the effects according to the above embodiments. According to the present embodiment, the heater 19 performs the refresh operation of burning adhered materials in the sensor 10S (110S, 210S). With the configuration, the adhered materials in the adsorption site are removed and thus the response speed of the sensor 10S (110S, 210S) is kept. Thereby, the response performance to the gas density is kept.

According to the present embodiment, the gas density measurement unit 30 measures the gas density on the basis of the parameters depending on the operating time of the sensor unit 10 (110, 210). With the configuration, the parameters depending on the deteriorated response performance of the sensor 10S (110S, 210S) are set, and thus the gas density can be accurately measured even if the response performance is deteriorated.

Eighth Embodiment

An eighth embodiment of the present invention will be described below. The above embodiments assume that the temperatures of the sensors are kept constant at the time of measurement of the gas density. That is, the values of the parameters k1, k2, and ΔVgmax at a predetermined temperature are used to measure the gas density.

However, the circumstances in the atmosphere such as temperature of the gas to be detected may rapidly change. In this case, the gas sensor may not keep the temperatures of the sensors constant even if the voltage of the heater is controlled. Then, the gas density cannot be accurately measured.

Thus, a gas sensor for accurately measuring a gas density even when the temperatures of the sensors vary will be described according to the present embodiment. The present embodiment is applied to any of the gas sensors described above. The description of the parts common with the above embodiments will be basically omitted below.

The gas sensor 1001 according to the present embodiment includes the sensor unit 10 (110, 210), the current measurement unit 20, the gas density measurement unit 30, the power supply unit 40, the control unit 50, the data I/O unit 90, and the parameter recording unit 1060 as illustrated in FIG. 21.

A sensor thermometer (not illustrated) for measuring the temperature of the sensor unit 10 (110, 210) is provided according to the present embodiment. The sensor thermometer is configured of a wiring a resistance value of which changes due to temperature, for example. The heater 19 can function as a sensor thermometer, for example.

The parameter recording unit 1060 records therein the information on temperature dependency of the parameters k1, k2, and ΔVgmax acquired in a previously-made test. For example, the parameter recording unit 1060 records therein, as the information on temperature dependency, a table, database or the like in which the temperature information of the sensor unit 10 (110, 210) is associated with the parameters k1, k2, and ΔVgmax. The parameter recording unit 1060 records therein a table, database or the like in which the temperature information is associated with the resistance value of the sensor thermometer (such as the heater 19). The parameter recording unit 1060 may record therein a table, database or the like in which the temperature, the resistance value of the sensor thermometer, and the values of the parameters k1, k2, and ΔVgmax are associated with each other.

For example, the gas density measurement unit 30 measures the resistance value of the heater 19 on the basis of the voltage applied between both ends of the heater 19 and the current of the heater 19 measured by the current measurement unit 20, for example, at the time of measurement of the gas density. The gas density measurement unit 30 then outputs the information on the resistance value of the heater 19 to the control unit 50. The control unit 50 reads the temperature information corresponding to the resistance value of the heater from the parameter recording unit 1060 on the basis of the information on the resistance value output from the gas density measurement unit 30. The control unit 50 reads the values of the corresponding parameters k1, k2, and ΔVgmax on the basis of the read temperature information. The control unit 50 outputs the read values of the parameters k1, k2, and ΔVgmax to the gas density measurement unit 30. The gas density measurement unit 30 measures the gas density on the basis of the output values of the parameters k1, k2, and ΔVgmax.

The following effects according to the present embodiment can be obtained in addition to the effects according to the above embodiments. According to the present embodiment, the sensor thermometer for measuring the temperature of the sensor unit 10 (110, 210) is provided and the gas density measurement unit 30 measures the gas density of the gas to be detected on the basis of the temperature of the sensor unit 10 (110, 210) and the parameters corresponding to the temperature of the sensor unit 10 (110, 210). With the configuration, the parameters are set depending on the temperature of the sensor unit 10 (110, 210), and thus the gas density can be accurately measured even under temperature-changing circumstances.

The sensor thermometer is configured of a wiring a resistance value of which changes due to temperature according to the present embodiment. With the configuration, the configuration of the sensor thermometer is simplified, thereby reducing cost required for the sensor thermometer.

The heater 19 functions as a sensor thermometer according to the present embodiment. With the configuration, the sensor thermometer may not be additionally provided, and an increase in size of the sensor unit 10 (110, 210) can be restricted.

Ninth Embodiment

A ninth embodiment of the present invention will be described below. The above embodiments do not consider an effect of other than gas to be detected at the time of measurement of the gas density. Generally, however, interference gas having an effect on the detection characteristic of gas to be detected by the gas sensor is present in the atmosphere. For example, when the gas to be detected is hydrogen gas, oxygen gas, water vapor, and the like are exemplary interference gas having an effect on the detection characteristic of the hydrogen gas. Thus, a gas sensor for accurately measuring the gas density of the gas to be detected even when interference gas is present in the atmosphere will be described according to the present embodiment. The present embodiment is applied to any of the gas sensors described above. The description of the parts common with the above embodiments will be basically omitted below.

Figure 22:
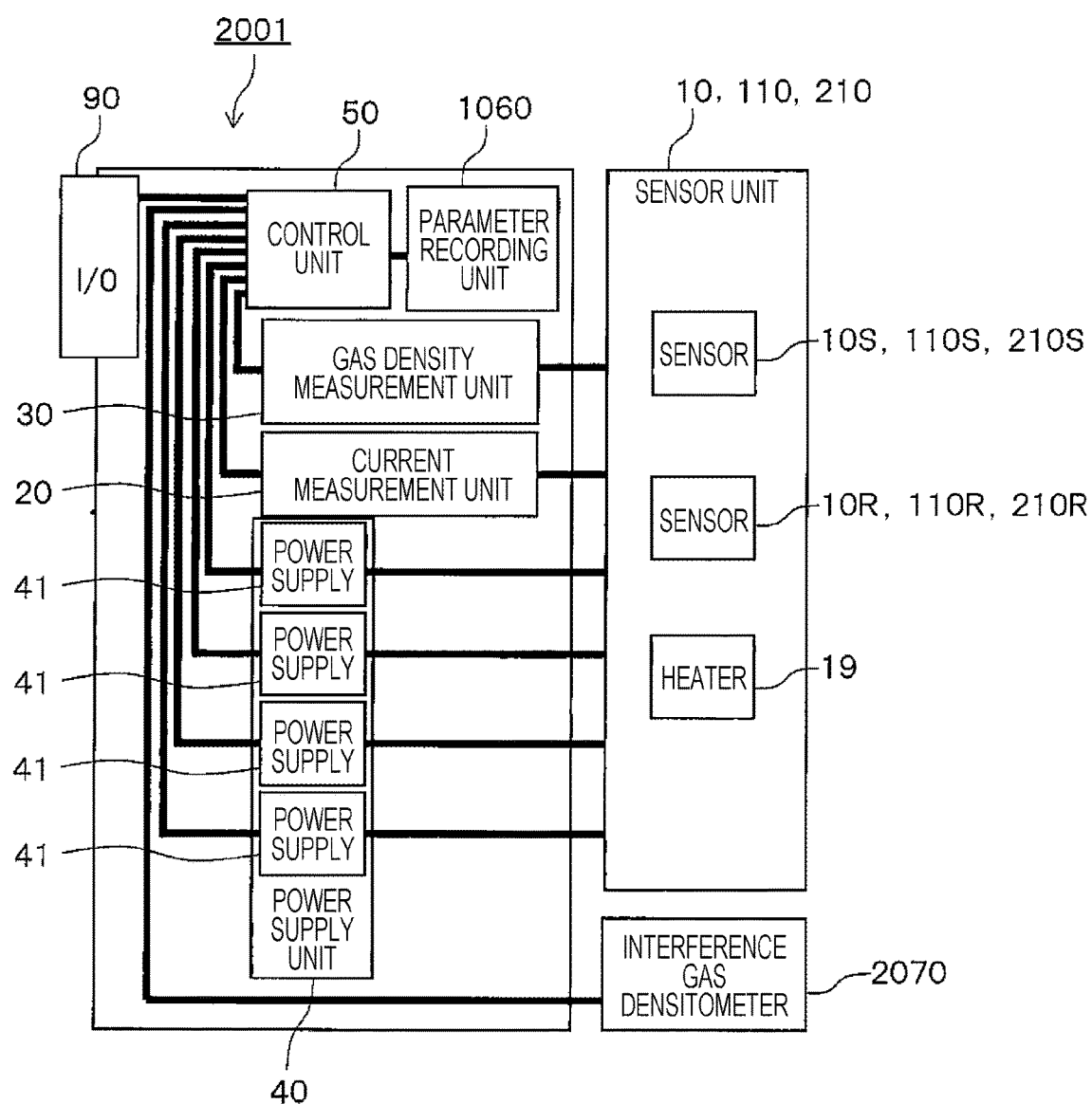
FIG. 22 is a diagram illustrating an exemplary configuration of a gas sensor according to a ninth embodiment of the present invention.

FIG. 22 is a diagram illustrating an exemplary configuration of a gas sensor according to the ninth embodiment of the present invention. A gas sensor 2001 according to the present embodiment includes the sensor unit 10 (110, 210), the current measurement unit 20, the gas density measurement unit 30, the power supply unit 40, the control unit 50, the data I/O unit 90, the parameter recording unit 1060, and an interference gas densitometer 2070 as illustrated in FIG. 22.

The parameter recording unit 1060 records therein the information on interference gas density dependency of the parameters k1, k2, and ΔVgmax acquired in a previously-made test, for example. For example, the parameter recording unit 1060 records therein, as the information on interference gas density dependency, a table, database, or the like in which the interference gas density information is associated with the values of the parameters k1, k2, and ΔVgmax.

The interference gas densitometer 2070 is configured of a gas sensor according to any of the above embodiments, for example. The interference gas densitometer 2070 measures a gas density of interference gas in the atmosphere. The interference gas densitometer 2070 then outputs the information on the measured gas density of the interference gas as interference gas density information to the control unit 50, for example. The control unit 50 reads the values of the parameters k1, k2, and ΔVgmax corresponding to the output interference gas density information from the parameter recording unit 1060. The control unit 50 then outputs the read values of the parameters k1, k2, and ΔVgmax to the gas density measurement unit 30. The gas density measurement unit 30 measures the gas density of the gas to be detected on the basis of the output values of the parameters k1, k2, and ΔVgmax. The interference gas densitometer 2070 may be connected to the gas density measurement unit 30 and may output the interference gas density information to the gas density measurement unit 30, for example. In this case, the control unit 50 reads the values of the parameters k1, k2, and ΔVgmax from the parameter recording unit 1060 on the basis of the interference gas density information output from the gas density measurement unit 30.

The parameter recording unit 1060 may record therein the information on temperature dependency and interference gas density dependency of the parameters k1, k2, and ΔVgmax acquired in a previously-made test, for example. For example, the parameter recording unit 1060 records therein, as the information on interference gas density dependency, a table, database, or the like in which the temperature information, the resistance value of the heater 19, the interference gas density information, and the values of the parameters k1, k2, and ΔVgmax are associated with each other.

In this case, the control unit 50 reads the temperature information corresponding to the measured resistance value of the heater 19 from the parameter recording unit 1060. The control unit 50 then reads the values of the parameters k1, k2, and ΔVgmax corresponding to the read temperature information and interference gas density information from the parameter recording unit 1060, and outputs them to the gas density measurement unit 30. The gas density measurement unit 30 measures the gas density on the basis of the output values of the parameters k1, k2, and ΔVgmax.

The following effects according to the present embodiment can be obtained in addition to the effects according to the above embodiments. The interference gas densitometer 2070 for measuring the gas density of interference gas having an effect on measurement of the gas density is provided according to the present embodiment. The gas density measurement unit 30 then measures the gas density of the gas to be detected on the basis of the gas density of the interference gas and the parameters corresponding to the gas density of the interference gas. With the configuration, an effect of the interference gas is considered, and thus the gas density of the gas to be detected can be accurately measured even when the interference gas is present.

According to the present embodiment, the gas density measurement unit 30 measures the gas density of the gas to be detected on the basis of the parameters corresponding to the temperature information and the interference gas density information. With the configuration, the temperature of the sensor unit 10 (110, 210) and an effect of the interference gas are considered, and thus the gas density of the gas to be detected can be more accurately measured even when the interference gas is present.

10th Embodiment

A 10th embodiment of the present invention will be described below. The method for reducing the response time of the gas sensor has been described according to the above embodiments. However, the activation time has a relationship with the response time in the gas sensor.

When the gas sensor 1 (101, 201, 1001, 2001) is activated, the sensors 10S (110S, 210S) and 10R (110R, 210R), and the heater 19 start being supplied with power. At this time, when the heat capacity of the sensor unit 10 (110, 210) is large, it may take a time for the sensor unit 10 (110, 210) to stabilize at a predetermined temperature even when Joule heat is generated from the heater 19. Then, the activation time of the gas sensor (101, 201, 1001, 2001) is longer. For example, the activation time after a hydrogen detector for fuel-cell vehicle is activated until the hydrogen gas density is accurately measured needs to be within one second, for example.

The gas sensor for reducing the activation time of the gas sensor will be described according to the present embodiment. The present embodiment is applied also to any of the above gas sensors. The description of the parts common with the above embodiments will be basically omitted below.

The gas sensor 1001 (2001) illustrated in FIGS. 21 and 22 will be described herein. When the gas sensor 1001 (2001) is activated to start supplying power to each unit in the sensor unit 10 (110, 210), the resistance value of the heater 19 is measured. For example, the control unit 50 reads the temperature information corresponding to the measured resistance value from the parameter recording unit 1060. The control unit 50 reads the values of the parameters k1, k2, and ΔVgmax corresponding to the read temperature information from the parameter recording unit 1060. The control unit 50 may assume the resistance value of the heater 19 as the temperature information, and may read the values of the parameters corresponding to the resistance value from the parameter recording unit 1060. The control unit 50 outputs the read values of the parameters to the gas density measurement unit 30. The gas density measurement unit 30 then measures the gas density on the basis of the output parameters. In this way, the gas sensor 1001 (2001) measures the gas density just after being activated.

The following effects according to the present embodiment can be obtained in addition to the effects according to the above embodiments. The gas density measurement unit 30 starts measuring the gas density within one second after the gas sensor is activated according to the present embodiment. With the configuration, the gas density is measured just after the gas sensor 1 is activated, and thus a time lag after the gas sensor is activated until the gas density is measured is reduced. Thereby, the gas sensor is widely used in various devices for which a reduction in activation time is required, such as hydrogen detector for fuel-cell vehicle.

The invention made by the present inventors has been specifically described above on the basis of the embodiments, but the present invention is not limited to the embodiments, and can be variously changed without departing from the sprit.

The present invention is not limited to the embodiments, and encompasses various variants. For example, the embodiments have been described in detail for simply explaining the present invention, and are not limited to ones including all the components described above.

Part of the components according to an embodiment may be replaced with the components according to other embodiment, and the components according to an embodiment may be added with the components according to other embodiment. Part of the components according to each embodiment may be added with, deleted, or replaced with other components. Each member and relative sizes in the Figures are simplified or ideally illustrated for simply explaining the present invention, and a more complicated shape may be mounted.

Main preferred forms of the present invention will be noted below.

[Note 1]

A gas sensor including:

a sensor unit including a first field-effect-transistor (FET)-type sensor, the first FET-type sensor including:

a first semiconductor substrate;

a first well formed on the first semiconductor substrate;

a first source diffusion layer formed on the first well;

a first drain diffusion layer formed on the first well;

a first gate insulative film formed on the first source diffusion layer and the first drain diffusion layer; and a first gate layer formed on the first gate insulative film in which at least part of a surface opposing the atmosphere is exposed;

a current measurement unit for measuring a first source-drain current flowing between the first source diffusion layer and the first drain diffusion layer; and a gas density measurement unit for measuring a gas density of gas to be detected in the atmosphere, wherein the gas density measurement unit measures the gas density of the gas to be detected at a predetermined time on the basis of a first threshold change as a difference between a first threshold voltage applied to the first gate layer when the first source-drain current is a predetermined threshold current while the gas to be detected is not present in the atmosphere and a second threshold voltage applied to the first gate layer when the first source-drain current is the predetermined threshold current at the predetermined time while the gas to be detected is present in the atmosphere, and a temporal differentiation of the first threshold change.

[Note 2]

The gas sensor according to note 1, wherein the first threshold voltage is applied to the first gate layer, and the gas density measurement unit calculates the first threshold change on the basis of a first well voltage applied to the first well when the first source-drain current is a predetermined threshold current while the gas to be detected is not present in the atmosphere and a second well voltage applied to the first well when the first source-drain current is the predetermined threshold current at a predetermined time while the gas to be detected is present in the atmosphere.

[Note 3]

A gas sensor including:

a sensor unit including a first capacitor-type sensor, the first capacitor-type sensor including:

a third semiconductor substrate;

a third well formed on the third semiconductor substrate;

a third gate insulative film formed on the third well; and a third gate layer formed on the third gate insulative film in which at least part of a surface opposing the atmosphere is exposed;

a current measurement unit for measuring a first gate current flowing in the third gate layer; and a gas density measurement unit for measuring a first capacitance of the first capacitor-type sensor on the basis of the first gate current and a voltage applied to the third gate layer, and measuring a gas density of gas to be detected in the atmosphere on the basis of the first capacitance, wherein a predetermined voltage is applied to the third well, and the gas density measurement unit measures the gas density of the gas to be detected at a predetermined time on the basis of a third threshold change as a difference between a fifth threshold voltage applied to the third gate layer when the first capacitance is a predetermined threshold capacitance while the gas to be detected is not present in the atmosphere and a sixth threshold voltage applied to the third gate layer when the first capacitance is the predetermined threshold capacitance at the predetermined time while the gas to be detected is present in the atmosphere, and a temporal differentiation of the third threshold change.

[Note 4]

The gas sensor according to note 3, wherein the gas density is expressed in the following Langmuir equation:

$$X = [\Delta V g \max \times (d \Delta V g(X)/dt) + k2 \times (\Delta V g(X))^n]/[k1 \times (\Delta V g \max - \Delta V g(X))^n]$$

where $\Delta Vg(X)$ indicates the third threshold change, $\Delta Vg\max$, k1, and k2 are parameters, and n indicates an index defined depending on the gas to be detected, and the gas density measurement unit measures the gas density on the basis of the Langmuir equation.

[Note 5]

The gas sensor according to note 4, wherein the Langmuir equation is derived assuming that an occupancy of the gas to be detected in an adsorption site of the third gate layer is proportional to the third threshold change.

[Note 6]

The gas sensor according to note 3, wherein a periodically-changing AC voltage is applied to the third well.

[Note 7]

The gas sensor according to note 3, including:

an operating time measurement unit for measuring an operating time of the sensor unit; and a parameter recording unit for recording the parameters corresponding to the operating time of the sensor unit, wherein the gas density measurement unit measures the gas density of the gas to be detected on the basis of the operating time of the sensor unit and the parameters corresponding to the operating time of the sensor unit.

[Note 8]

The gas sensor according to note 3, wherein the sensor unit includes a second capacitor-type sensor, the second capacitor-type sensor including:

a fourth semiconductor substrate;

a fourth well formed on the fourth semiconductor substrate;

a fourth gate insulative film formed on the fourth well;

a fourth gate layer formed on the fourth gate insulative film; and a second gate protective film formed to cover an entire surface of the fourth gate layer opposing the atmosphere, the current measurement unit measures a second gate current flowing in the fourth gate layer, the gas density measurement unit measures a second capacitance of the second capacitor-type sensor on the basis of the second gate current and a voltage applied to the fourth gate layer, and measures a gas density of gas to be detected in the atmosphere on the basis of the first capacitance and the second capacitance, the predetermined voltage is applied to the fourth well, and the gas density measurement unit measures the gas density of the gas to be detected at a predetermined time on the basis of a fourth threshold change as a difference between a third inter-sensor potential difference as a difference between a seventh threshold voltage applied to the fourth gate layer when the second capacitance is the predetermined threshold capacitance and the fifth threshold voltage while the gas to be detected is not present in the atmosphere and a fourth inter-sensor potential difference as a difference between an eighth threshold voltage applied to the fourth gate layer when the second capacitance is the predetermined threshold capacitance at the predetermined time and the sixth threshold voltage while the gas to be detected is present in the atmosphere, and a temporal differentiation of the fourth threshold change.

[Note 9]

The gas sensor according to note 8, wherein the gas density is expressed in the following Langmuir equation:

$X=[\Delta Vgmax \times (d\Delta Vg(X)/dt)+k2\times(\Delta Vg(X))^n]/[k1\times(\Delta Vgmax-\Delta Vg(X))^n]$ where ΔVg(X) indicates the fourth threshold change, ΔVgmax, k1, and k2 are parameters, and n indicates an index defined depending on the gas to be detected, and the gas density measurement unit measures the gas density on the basis of the Langmuir equation.

[Note 10]

The gas sensor according to note 8, wherein a periodically-changing AC voltage is applied to the third well and the fourth well.

[Note 11]

A gas sensor including:

a sensor unit including a first diode-type sensor, the first diode-type sensor including:

a fifth semiconductor substrate;

a fifth well formed on the fifth semiconductor substrate; and a fifth gate layer formed on the fifth well in which at least part of a surface opposing the atmosphere is exposed, a current measurement unit for measuring a first diode current flowing between the fifth gate layer and the fifth well; and a gas density measurement unit for measuring a gas density of gas to be detected in the atmosphere, wherein the gas density measurement unit measures the gas density of the gas to be detected at a predetermined time on the basis of a fifth threshold change as a difference between a ninth threshold voltage applied to the fifth gate layer when the first diode current is a second threshold current while the gas to be detected is not present in the atmosphere and a tenth threshold voltage applied to the fifth gate layer when the first diode current is the second threshold current at the predetermined time while the gas to be detected is present in the atmosphere, and a temporal differentiation of the fifth threshold change.

[Note 12]

The gas sensor according to note 11, wherein the gas density is expressed in the following Langmuir equation:

$X=[\Delta Vgmax \times (d\Delta Vg(X)/dt)+k2\times(\Delta Vg(X))^n]/[k1\times(\Delta Vgmax-\Delta Vg(X))^n]$ where ΔVg(X) indicates the fifth threshold change, ΔVgmax, k1, and k2 are parameters, and n indicates an index defined depending on the gas to be detected, and the gas density measurement unit measures the gas density on the basis of the Langmuir equation.

[Note 13]

The gas sensor according to note 12, wherein the Langmuir equation is derived assuming that an occupancy of the gas to be detected in an adsorption site of the fifth gate layer is proportional to the fifth threshold change.

[Note 14]

The gas sensor according to note 11, wherein the sensor unit includes a second diode-type sensor, the second diode-type sensor including:

a sixth semiconductor substrate;

a sixth well formed on the sixth semiconductor substrate;

a sixth gate layer formed on the sixth well; and a second gate protective film formed to cover an entire surface of the sixth gate layer opposing the atmosphere, the current measurement unit measures a second diode current flowing between the sixth gate layer and the sixth well, and the gas density measurement unit measures the gas density of the gas to be detected at a predetermined time on the basis of a sixth threshold change as a difference between a fifth inter-sensor potential difference as a difference between an 11th threshold voltage applied to the sixth gate layer when the second diode current is the second threshold current and the ninth threshold voltage while the gas to be detected is not present in the atmosphere and a sixth inter-sensor potential difference as a difference between a 12th threshold voltage applied to the sixth gate layer when the second diode current is the second threshold current at the predetermined time and the 10th threshold voltage while the gas to be detected is present in the atmosphere, and a temporal differentiation of the sixth threshold change.

[Note 15]

The gas sensor according to note 14, wherein the gas density is expressed in the following Langmuir equation:

$X=[\Delta Vgmax \times (d\Delta Vg(X)/dt)+k2\times(\Delta Vg(X))^n]/[k1\times(\Delta Vgmax-\Delta Vg(X))^n]$ where ΔVg(X) indicates the sixth threshold change, ΔVgmax, k1, and k2 are parameters, and n indicates an index defined depending on the gas to be detected, and the gas density measurement unit measures the gas density on the basis of the Langmuir equation.

[Note 16]

The gas sensor according to note 15, wherein the Langmuir equation is derived assuming that an occupancy of the gas to be detected in an adsorption site of the fifth gate layer is proportional to the sixth threshold change.

What is claimed is:

1. A gas sensor comprising:
a sensor unit comprising a first field-effect-transistor (FET)-type sensor, the first FET-type sensor comprising:
a first semiconductor substrate;
a first well formed on the first semiconductor substrate;
a first source diffusion layer formed on the first well;
a first drain diffusion layer formed on the first well;
a first gate insulative film formed on the first source diffusion layer and the first drain diffusion layer; and
a first gate layer formed on the first gate insulative film in which at least part of a surface opposing the atmosphere is exposed; and
the sensor unit is configured to:
measure a first source-drain current flowing between the first source diffusion layer and the first drain diffusion layer, and
measure a gas density of gas to be detected in the atmosphere,
wherein the gas density of the gas to be detected is measured at a predetermined time on the basis of a first threshold change as a difference between a first threshold voltage applied to the first gate layer when the first source-drain current is a first threshold current while the gas to be detected is not present in the atmosphere and a second threshold voltage applied to the first gate layer when the first source-drain current is the first threshold current at the predetermined time while the gas to be detected is present in the atmosphere, and a temporal differentiation of the first threshold change.

2. The gas sensor according to claim 1,
wherein the gas density is expressed in the following Langmuir equation:

$$X=[\Delta Vg\max \times (d\Delta Vg(X)/dt)+k2\times(\Delta Vg(X))^n]/[k1\times(\Delta Vg\max-\Delta Vg(X))^n]$$

where $\Delta Vg(X)$ indicates the first threshold change, $\Delta Vg\max$, k1, and k2 are parameters, and n indicates an index defined depending on the gas to be detected, and
the sensor unit is configured to measure the gas density on the basis of the Langmuir equation.

3. The gas sensor according to claim 2,
wherein the sensor unit is configured to set the index in the Langmuir equation depending on the kind of the gas to be detected, and measures the gas density.

4. The gas sensor according to claim 3,
wherein the first gate layer is configured such that an electrode support layer made of titanium oxide and an electrode layer made of platinum are laminated, and
the sensor unit is configured to set the index in the Langmuir equation depending on the number of hydrogen atoms in the molecules of the gas to be detected.

5. The gas sensor according to claim 3,
wherein the first gate layer is configured such that an electrode support layer made of yttria-stabilized zirconia and an electrode layer made of platinum are laminated, and
the sensor unit is configured to set the index in the Langmuir equation depending on the number of oxygen atoms in the molecules of the gas to be detected.

6. The gas sensor according to claim 2, comprising:
the sensor unit is configured to:
  measure an operating time of the first FET-type sensor,
  record parameters corresponding to the operating time of the sensor unit, and
  measure the gas density of the gas to be detected on the basis of the operating time of the first FET-type sensor and the recorded parameters.

7. The gas sensor according to claim 2, comprising:
a sensor thermometer for measuring a temperature of the first FET-type sensor; and
the sensor unit is configured to:
  record parameters corresponding to the temperature of the sensor unit, and
  measure the gas density of the gas to be detected on the basis of the temperature of the sensor unit and the parameters corresponding to the temperature of the sensor unit.

8. The gas sensor according to claim 7,
wherein the sensor thermometer comprises a wiring with a resistance value of that changes due to temperature.

9. The gas sensor according to claim 2, comprising
an interference gas densitometer for measuring a gas density of interference gas having an effect on measurement of the gas density of the gas to be detected; and
the sensor unit configured to:
  record parameters corresponding to the gas density of the interference gas, and
  measure the gas density of the gas to be detected on the basis of the gas density of the interference gas and the parameters corresponding to the gas density of the interference gas.

10. The gas sensor according to claim 1,
further comprising a heater.

11. The gas sensor according to claim 10,
wherein the heater performs a refresh operation of burning adhered materials on the first FET-type sensor.

12. The gas sensor according to claim 1,
wherein the sensor unit is configured to measure the gas density of the gas to be detected at a predetermined interval.

13. The gas sensor according to claim 1,
wherein the sensor unit comprises a second FET-type sensor, the second FET-type sensor comprising:
  a second semiconductor substrate;
  a second well formed on the second semiconductor substrate;
  a second source diffusion layer formed on the second well;
  a second drain diffusion layer formed on the second well;
  a second gate insulative film formed on the second source diffusion layer and the second drain diffusion layer;
  a second gate layer formed on the second gate insulative film; and
  a first gate protective film formed to cover an entire surface of the second gate layer opposing the atmosphere; and
the sensor unit is configured to:
  measure a second source-drain current flowing between the second source diffusion layer and the second drain diffusion layer, and
  measure the gas density of the gas to be detected at a predetermined time on the basis of a second threshold change as a difference between a first inter-sensor potential difference as a difference between a third threshold voltage applied to the second gate layer when the second source-drain current is the first threshold current and the first threshold voltage while the gas to be detected is not present in the atmosphere, and a second inter-sensor potential difference as a difference between a fourth threshold voltage applied to the second gate layer when the second source-drain current is the first threshold current at the predetermined time and the second threshold voltage while the gas to be detected is present in the atmosphere, and a temporal differentiation of the second threshold change.

14. The gas sensor according to claim 13,
wherein the gas density is expressed in the following Langmuir equation:

$$X=[\Delta Vg\max \times (d\Delta Vg(X)/dt)+k2\times(\Delta Vg(X))^n]/[k1\times(\Delta Vg\max-\Delta Vg(X))^n]$$

where $\Delta Vg(X)$ indicates the second threshold change, $\Delta Vg\max$, k1, and k2 are parameters, and n indicates an index defined depending on the gas to be detected, and
the sensor unit is configured to measure the gas density on the basis of the Langmuir equation.

15. The gas sensor according to claim 1,
wherein the sensor unit is configured to:
  measure a predetermined current as the first source-drain current when the first threshold voltage is applied to the first gate layer while the gas to be detected is present in the atmosphere,
  detect a predetermined voltage applied to the first gate layer when the first source-drain current is the predetermined current while the gas to be detected is not present in the atmosphere, and calculate the first threshold change on the basis of the predetermined voltage and the first threshold voltage.

* * * * *